(12) United States Patent
Zhang et al.

(10) Patent No.: US 11,986,477 B2
(45) Date of Patent: May 21, 2024

(54) DRUG COMBINATION AND USE FOR TREATING TUMORS

(71) Applicant: INXMED (NANJING) CO., LTD., Nanjing (CN)

(72) Inventors: Baoyuan Zhang, Shanghai (CN); Xuebin Liu, Nanjing (CN); Jiaming Gao, Shanghai (CN); Ping Zhang, Nanjing (CN); Ran Pang, Nanjing (CN); Zaiqi Wang, Shanghai (CN)

(73) Assignee: INXMED (NANJING) CO., LTD., Nanjing (CN)

( * ) Notice: Subject to any disclaimer, the term of this patent is extended or adjusted under 35 U.S.C. 154(b) by 0 days.

(21) Appl. No.: 18/387,180

(22) Filed: Nov. 6, 2023

(65) Prior Publication Data
US 2024/0082247 A1    Mar. 14, 2024

Related U.S. Application Data

(63) Continuation of application No. PCT/CN2023/101720, filed on Jun. 21, 2023.

(30) Foreign Application Priority Data

Jun. 24, 2022   (CN) .......................... 202210730136.2

(51) Int. Cl.
*A61K 31/506*   (2006.01)
*A61P 35/00*    (2006.01)

(52) U.S. Cl.
CPC ............ *A61K 31/506* (2013.01); *A61P 35/00* (2018.01)

(58) Field of Classification Search
CPC .............................. A61K 31/506; A61P 35/00
USPC .......................................................... 514/272
See application file for complete search history.

(56) References Cited

FOREIGN PATENT DOCUMENTS

| | | |
|---|---|---|
| CN | 102292322 A | 12/2011 |
| CN | 108289892 A | 7/2018 |
| WO | 2021098679 A1 | 5/2021 |
| WO | 2021104454 A1 | 6/2021 |
| WO | WO-2021154929 A1 * | 8/2021 ........... A61K 31/506 |
| WO | 2022028367 A1 | 2/2022 |

OTHER PUBLICATIONS

International Search Report issued in PCT/CN2023/101720, mailed Sep. 27, 2023, 4 pages. Chinese with English translation.

* cited by examiner

*Primary Examiner* — Yevgeny Valenrod
(74) *Attorney, Agent, or Firm* — K&L Gates LLP

(57) ABSTRACT

The present disclosure relates to the combination of IN10018 and an epidermal growth factor receptor tyrosine kinase inhibitor for the treatment of tumors.

15 Claims, 5 Drawing Sheets

| Negative control | IN10018 | AZD9291 | AZD9291+IN10018 |
|---|---|---|---|
|  |  |  |  |

| Negative control | IN10018 | Almonertinib | Almonertinib +IN10018 |
|---|---|---|---|
|  |  |  |  |

DRUG COMBINATION AND USE FOR TREATING TUMORS

This application is a continuation application filed under 35 U.S.C. 111(a) of PCT/CN2023/101720, filed Jun. 21, 2023, which claims the priority of the Chinese Patent Application No. 202210730136.2 filed on Jun. 24, 2022. The above-identified applications are incorporated herein by reference as part of the disclosure of the present application.

FIELD OF THE INVENTION

The present disclosure belongs to the field of medicinal chemistry. Specifically, the present disclosure relates to the use of the Focal Adhesion Kinase (FAK) inhibitor IN10018 in combination with another antitumor agent for the treatment of tumors.

BACKGROUND OF THE INVENTION

EGFR is known as Epidermal Growth Factor Receptor. The EGFR gene is responsible for encoding and making a receptor protein called the epidermal growth factor receptor. The EGFR receptor protein is a transmembrane protein that is divided into three parts: one end of the protein located outside the cell, one part located in the cell membrane, and the other end located inside the cell. This allows the EGFR receptor to bind to other proteins outside the cell (called ligands) to help the cell receive signals and respond to its stimuli. The binding of receptor to ligand is like a key to a lock, so they each have a specific binding "partner". When EGFR binds to a ligand, it attaches to another EGFR receptor located nearby and forms a complex (dimer), which enters an activated state and activates intracellular signaling pathways. EGFR mutations mainly occur in exons 18~21, of which deletion mutation of exon 19 and L858R point mutation of exon 21 are the most common types of mutations, accounting for 90% of all mutation types. When pathogenic mutations occur in EGFR, the EGFR receptor protein is continuously activated, which leads to cells continuously receiving signals for proliferation and survival, results in excessive cell growth and survival (failure to apoptosis properly), and induces tumor formation.

Targeted drugs currently available for EGFR mutations include: the first-generation icotinib, gefitinib and erlotinib for exon 19 and 21 mutations; the second-generation afatinib for exon 8 and 20 mutations and the third-generation osimertinib (also known as AZD9291 herein), almonertinib, and alflutinib for T790M mutations. Targeted drugs for ALK mutations include: the first-generation targeted drug crizotinib, the second-generation targeted drugs ceritinib, alectinib and brigatinib, and the third-generation targeted drug lorlatinib. However, resistance to these targeted drugs often appears about 1 year after administration. Overcoming resistance to targeted drugs or delaying the resistance emergence is the main goal of antineoplastic drug development.

SUMMARY OF THE INVENTION

In one aspect, the present disclosure provides use of IN10018 or a pharmaceutically acceptable salt thereof and an epidermal growth factor receptor tyrosine kinase inhibitor in the manufacture of a medicament for the treatment of a tumor in a subject, the IN10018 having a structure of:

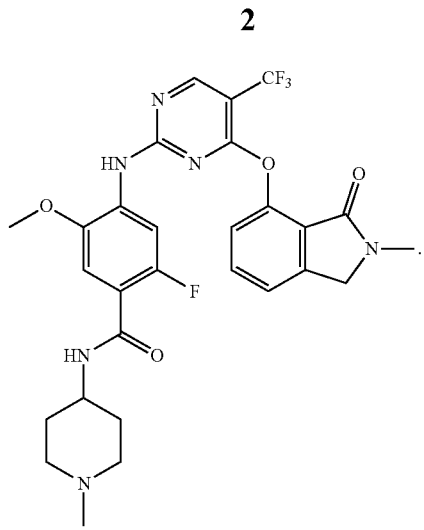

In another aspect, the present disclosure provides a pharmaceutical combination product of IN10018 or a pharmaceutically acceptable salt thereof and an epidermal growth factor receptor tyrosine kinase inhibitor, for use in the treatment of a tumor in a subject.

In another aspect, the present disclosure provides a method of treating a tumor, which comprises administering to a subject in need thereof a therapeutically effective amount of IN10018 or a pharmaceutically acceptable salt thereof and an epidermal growth factor receptor tyrosine kinase inhibitor.

In another aspect, the present disclosure provides a kit or pharmaceutically acceptable composition comprising: (a) IN10018 or a pharmaceutically acceptable salt thereof; and (b) an epidermal growth factor receptor tyrosine kinase inhibitor.

In another aspect, the present disclosure provides use of IN10018 or a pharmaceutically acceptable salt thereof and an epidermal growth factor receptor tyrosine kinase inhibitor in the manufacture of a combination medicament for the treatment of a tumor.

In another aspect, the present disclosure provides use of IN10018 or a pharmaceutically acceptable salt thereof in the manufacture of a medicament for use in combination with an epidermal growth factor receptor tyrosine kinase inhibitor for the treatment of a tumor.

In another aspect, the present disclosure provides use of an epidermal growth factor receptor tyrosine kinase inhibitor in the manufacture of a medicament for use in combination with IN10018 or a pharmaceutically acceptable salt thereof for the treatment of a tumor.

In another aspect, the present disclosure provides a kit comprising: IN10018 or a pharmaceutically acceptable salt thereof; and instructions stating that the IN10018 or pharmaceutically acceptable salt thereof can be used in combination with an epidermal growth factor receptor tyrosine kinase inhibitor for the treatment of a tumor.

In another aspect, the present disclosure provides a kit comprising: an epidermal growth factor receptor tyrosine kinase inhibitor; and instructions stating that the epidermal growth factor receptor tyrosine kinase inhibitor can be used in combination with IN10018 or a pharmaceutically acceptable salt thereof for the treatment of a tumor.

In another aspect, the present disclosure provides a method of treating a tumor, the method comprising administering to a subject in need thereof a therapeutically effective amount of IN10018 or a pharmaceutically acceptable salt thereof and an epidermal growth factor receptor tyrosine kinase inhibitor.

In another aspect, the present disclosure provides a pharmaceutical combination product of IN10018 or a pharmaceutically acceptable salt thereof and an epidermal growth factor receptor tyrosine kinase inhibitor, for use in the treatment of a tumor in a subject in need thereof.

Optionally, the pharmaceutically acceptable salt of the IN10018 is tartrate salt of the IN10018.

Optionally, the epidermal growth factor receptor tyrosine kinase inhibitor is Gefitinib, Erlotinib, Icotinib, Afatinib, Crizotinib, Osimertinib (AZD9291), Almonertinib, Alflutinib (also known as Furmonertinib), EAI045, JBJ-25-02, BLU945, BLU701, TQB3804, BBT-176, ES-072, BPI-361175, CH7233163, or a pharmaceutically acceptable salt thereof, preferably Osimertinib, Almonertinib, Alflutinib, or a pharmaceutically acceptable salt thereof.

The CAS No. of Gefitinib is 184475-35-2. The CAS No. of Erlotinib is 183321-74-6. The CAS No. of Icotinib is 610798-31-7. The CAS No. of Afatinib is 850140-72-6. The CAS No. of Crizotinib is 877399-52-5. The CAS No. of Osimertinib (AZD9291) is 1421373-65-0. The CAS No. of Almonertinib is 1899921-05-1. The CAS No. of Alflutinib (also known as Furmonertinib) is 1869057-83-9. The CAS No. of EAI045 is 1942114-09-1. The CAS No. of JBJ-04-125-02 is 2060610-53-7. The CAS No. of BLU945 is 2660250-10-0; BLU701 is jointly developed by Blueprint Medicines Corp. and Zai Lab. The CAS No. of TQB3804 is 2267329-76-8. BBT-176 is developed by Bridge Biotherapeutics. ES-072 is developed by Bossan Pharmaceutical Co., Ltd. BPI-361175 is developed by Betta Pharmaceuticals Co., Ltd. CH7233163 is developed by Chugai Pharmaceutical Co., Ltd.

Optionally, the IN10018 or a pharmaceutically acceptable salt thereof and the epidermal growth factor receptor tyrosine kinase inhibitor are administered simultaneously or sequentially to the subject.

Optionally, the tumor is selected from bladder cancer, breast cancer, cervical cancer, colon cancer (including colorectal cancer), esophageal cancer, esophageal squamous cell carcinoma, head and neck cancer, liver cancer, lung cancer (including small cell lung cancer and non-small cell lung cancer), melanoma, myeloma, rhabdomyosarcoma, inflammatory myofibroblastic tumor, neuroblastoma, pancreatic cancer, prostate cancer, kidney cancer, renal cell carcinoma, sarcoma (including osteosarcoma), skin cancer (including squamous cell carcinoma), gastric cancer, testicular cancer, thyroid cancer, uterine cancer, mesothelioma, cholangiocarcinoma, leiomyosarcoma, liposarcoma, nasopharyngeal carcinoma, neuroendocrine carcinoma, ovarian cancer, salivary gland cancer, metastasis caused by spindle cell carcinoma, anaplastic large cell lymphoma, thyroid undifferentiated carcinoma, non-Hodgkin's lymphoma, Hodgkin's lymphoma, neuroglioma, and hematological malignancies, such as acute myeloid leukemia (AML), acute lymphoblastic leukemia (ALL), diffuse large B-cell lymphoma (DLBCL), follicular lymphoma (FL), chronic lymphocytic leukemia (CLL), and chronic myeloid leukemia (CML); alternatively, wherein the tumor is lung cancer, breast cancer, neuroglioma, esophageal cancer, head and neck cancer or colorectal cancer; alternatively, the tumor is lung cancer or colorectal cancer.

BRIEF DESCRIPTION OF THE DRAWINGS

In order to illustrate the technical solutions of the examples of the present disclosure more clearly, the drawings of the examples will be briefly introduced below. Apparently, the drawings in the following description only relate to some examples of the present disclosure, rather than limiting the present disclosure.

DETAILED DESCRIPTION OF THE INVENTION

Figures 1, 2, 3:
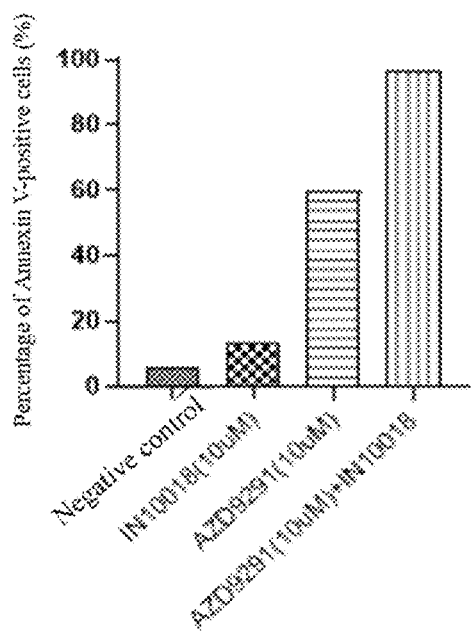
FIG. 1 shows white light micrographs of cells taken after incubation of Example 1 lung cancer KPL cells with the drug for 48 hours.
FIG. 2 shows the percentage of annexin V-positive KPL cells after incubation of Example 1 lung cancer KPL cells with the drug for 48 hours.
FIG. 3 shows white light micrographs of cells taken after incubation of Example 2 lung cancer KPL cells with the drug for 48 hours.

In order to make the purpose, technical solutions and advantages of the examples of the present disclosure clearer, the technical solutions of the examples of the present disclosure will be clearly and completely described below in conjunction with the drawings of the examples of the present disclosure. Apparently, the described examples are a part of the examples of the present disclosure, not all of the examples of the present disclosure. Based on the described examples of the present disclosure, all other examples obtained by those of ordinary skill in the art without creative effort shall fall within the protection scope of the present invention.

The present disclosure may be embodied in other specific forms without departing from essential attributes of the present disclosure. It should be understood that any and each embodiment of the present disclosure can be combined with technical feature(s) in another embodiment or other embodiments to obtain additional embodiments under the premise of no conflict. Additional embodiments resulting from such combinations are also included by the present disclosure.

All publications and patents mentioned in this disclosure are hereby incorporated by reference into this disclosure in their entirety. If usage or terminology used in any publications and patents incorporated by reference conflicts with usage or terminology used in the present disclosure, the usage and terminology in the present disclosure shall control.

The section headings used herein are for the purpose of organizing the article only and should not be construed as limitations on the subject matter described.

Unless defined otherwise, all technical and scientific terms used herein have their ordinary meanings in the art to which the claimed subject matter belongs. In the event that more than one definition exists for a term, the definition herein controls.

Except in the working examples or where otherwise indicated, all numbers expressing quantitative properties, such as dosage, stated in the specification and claims are to be understood as being modified by the term "about" in all instances. It should also be understood that any numerical range recited herein is intended to include any combination of all subranges within that range and the respective endpoints of that range or subrange.

The words "comprising", "including" or "containing" and similar words used in the present disclosure mean that an element appearing before the words covers elements listed after the words and equivalents thereof and does not exclude any unrecited element. The term "comprising" or "including (containing)" used herein can be open, semi-closed and closed. In other words, the term also includes "consisting essentially of" or "consisting of".

Definitions

The following terms and symbols used in this application have the meanings set forth below, unless their context indicates otherwise.

As used herein, the term "epidermal growth factor receptor tyrosine kinase inhibitor" refers to an agent that selectively and effectively inhibits epidermal growth factor receptor tyrosine kinase. Examples of the epidermal growth factor receptor tyrosine kinase inhibitors include, but are not limited to Gefitinib, Erlotinib, Icotinib, Afatinib, Crizotinib, Osimertinib (AZD9291), Almonertinib, Alflutinib (also known as Furmonertinib), EAI045, JBJ-25-02, BLU945, BLU701, TQB3804, BBT-176, ES-072, BPI-361175, CH7233163, or a pharmaceutically acceptable salt thereof. In some embodiments, the epidermal growth factor receptor tyrosine kinase inhibitor is Osimertinib, Almonertinib, Alflutinib, or a pharmaceutically acceptable salt thereof.

The CAS No. of Gefitinib is 184475-35-2. The CAS No. of Erlotinib is 183321-74-6. The CAS No. of Icotinib is 610798-31-7. The CAS No. of Afatinib is 850140-72-6. The CAS No. of Crizotinib is 877399-52-5. The CAS No. of Osimertinib (AZD9291) is 1421373-65-0. The CAS No. of Almonertinib is 1899921-05-1. The CAS No. of Alflutinib (also known as Furmonertinib) is 1869057-83-9. The CAS No. of EAI045 is 1942114-09-1. The CAS No. of JBJ-04-125-02 is 2060610-53-7. The CAS No. of BLU945 is 2660250-10-0; BLU701 is jointly developed by Blueprint Medicines Corp. and Zai Lab. The CAS No. of TQB3804 is 2267329-76-8. BBT-176 is developed by Bridge Biotherapeutics. ES-072 is developed by Bossan Pharmaceutical Co., Ltd. BPI-361175 is developed by Betta Pharmaceuticals Co., Ltd. CH7233163 is developed by Chugai Pharmaceutical Co., Ltd.

As used herein, "drug combination" or "drug combination product" can refer to either a fixed combination in the form of one dosage unit (e.g., all active ingredients present in one dosage form) or a kit to administer the product in combination, or a combination of a drug and instructions indicating that the drug can be used in combination with one or more other drugs.

The term "combined treatment" or "combination medicament" as used herein refers to the use of a drug in combination with one or more other drugs to treat a disease and includes both the combination of a drug with one or more other drugs and the combination of a drug with instructions indicating that the drug can be used in combination with one or more other drugs.

"Simultaneous or sequential administration" in this application means that two or more drugs are administered simultaneously or sequentially at certain intervals within a dosing cycle (e.g., within 4 weeks, 3 weeks, 2 weeks, 1 week, or within 24 hours), and their mode of administration (e.g., oral, intravenous, intramuscular, or subcutaneous) can be the same or different, and the frequency/cycle of administration of the two or more drugs can be the same or different. When the therapeutic method, product, or use of the present disclosure involves two drugs, the two drugs may be administered at the same time or separately at certain time intervals.

The term "treats", "treating", or "treatment" as used herein refers to the administration of one or more drugs to an individual with a disease or symptoms of the disease, to cure, alleviate, reduce, alter, remedy, ameliorate, improve or affect the disease or the symptoms of the disease. In some embodiments, the disease is a tumor or cancer.

The term "tumor" as used herein refers to an abnormal lesion formed by abnormally clonal proliferation of cells of local tissues which lose the normal regulation on their growth at the gene level under the action of various tumorigenic factors. Examples include, but are not limited to: bladder cancer, breast cancer, cervical cancer, colon cancer (including colorectal cancer), esophageal cancer, esophageal squamous cell carcinoma, head and neck cancer, liver cancer, lung cancer (including small cell lung cancer and non-small cell lung cancer), melanoma, myeloma, rhabdomyosarcoma, inflammatory myofibroblastic tumor, neuroblastoma, pancreatic cancer, prostate cancer, kidney cancer, renal cell carcinoma, sarcoma (including osteosarcoma), skin cancer (including squamous cell carcinoma), gastric cancer, testicular cancer, thyroid cancer, uterine cancer, mesothelioma, cholangiocarcinoma, leiomyosarcoma, liposarcoma, nasopharyngeal carcinoma, neuroendocrine carcinoma, ovarian cancer, salivary gland cancer, metastasis caused by spindle cell carcinoma, anaplastic large cell lymphoma, thyroid undifferentiated carcinoma, non-Hodgkin's lymphoma, Hodgkin's lymphoma, neuroglioma, and hematological malignancies, such as acute myeloid leukemia (AML), acute lymphoblastic leukemia (ALL), diffuse large B-cell lymphoma (DLBCL), follicular lymphoma (FL), chronic lymphocytic leukemia (CLL), and chronic myeloid leukemia (CML); alternatively, wherein the tumor is lung cancer, breast cancer, neuroglioma, esophageal cancer, head and neck cancer or colon cancer; alternatively, the tumor is lung cancer or colon cancer.

As used herein, the term "individual" or "subject" refers to mammals and non-mammals. Mammals means any member of the mammalian class including, but not limited to, humans; non-human primates such as chimpanzees and other apes and monkey species; farm animals such as cattle, horses, sheep, goats, and swines; domestic animals such as rabbits, dogs, and cats; laboratory animals including rodents, such as rats, mice, and guinea pigs; and the like. Examples of non-mammals include, but are not limited to, birds, and the like. The term "individual" does not denote a particular age or sex. In some embodiments, the individual is a human.

As used herein, the term "pharmaceutically acceptable" means non-toxic, biologically tolerable and suitable for administration to an individual.

As used herein, the term "pharmaceutically acceptable salt" refers to an acid addition salt that is non-toxic, biologically tolerable and suitable for administration to an individual, which includes, but are not limited to, acid addition salts with an inorganic acid, such as hydrochloride, hydrobromide, carbonate, bicarbonate, phosphate, sulfate, sulfite, nitrate, and the like; and acid addition salts with an organic acid, such as formate, acetate, malate, maleate, fumarate, tartrate, succinate, citrate, lactate, methanesulfonate, p-toluenesulfonate, 2-hydroxyethanesulfonate, benzoate, salicylate, stearate, and salts with alkane-dicarboxylic acid of formula HOOC—$(CH_2)_n$—COOH (wherein n is 0-4), etc.

In addition, a pharmaceutically acceptable acid addition salt may be produced by dissolving the free base in a suitable solvent and treating the solution with an acid, in accordance with conventional procedures for preparing acid addition salts from basic compounds. Those skilled in the art can determine, without undue experimentation, a variety of synthetic methods, which are used to prepare non-toxic pharmaceutically acceptable acid addition salts. In some embodiments, the pharmaceutically acceptable salt of the IN10018 is a tartrate salt.

As used herein, the term "pharmaceutically acceptable composition" means that it must be chemically and/or toxicologically compatible with the other ingredients comprised by the formulation and/or with the subject receiving the treatment. The term "therapeutically effective amount" as used herein refers to an amount that is generally sufficient to produce a beneficial therapeutic effect on the subject. The therapeutically effective amount of the present disclosure can be determined by conventional methods (e.g., modeling, dose-escalation studies, or clinical trials) in combination with conventional influencing factors (e.g., mode of administration, pharmacokinetics of the compound, severity and duration of the disease, medical history of the subject, health status of the subject, responsiveness of the subject to the drug, etc.).

As used herein, the term "inhibits", "inhibiting", or "inhibition" refers to a reduction in baseline activity of a biological function or process.

The term "kit" as used herein refers to a box for holding chemical reagents for the detection of chemical components, drug residues, virus species, etc. The kit described herein may comprise (i) one or two of IN10018 or a pharmaceutically acceptable salt thereof and an epidermal growth factor receptor tyrosine kinase inhibitor; and (ii) instructions stating that the IN10018 or a pharmaceutically acceptable salt thereof and the epidermal growth factor receptor tyrosine kinase inhibitor can be used to treat a tumor in a subject. In one embodiment, the kit comprises (i) IN10018 or a pharmaceutically acceptable salt thereof; and (ii) instructions stating that the IN10018 or a pharmaceutically acceptable salt thereof and the epidermal growth factor receptor tyrosine kinase inhibitor can be used to treat a tumor in a subject. In one embodiment, the kit comprises (i) an epidermal growth factor receptor tyrosine kinase inhibitor; and (ii) instructions stating that IN10018 or a pharmaceutically acceptable salt thereof and the epidermal growth factor receptor tyrosine kinase inhibitor can be used to treat the tumor in the subject. In one embodiment, the kit comprises (i) IN10018 or a pharmaceutically acceptable salt thereof and an epidermal growth factor receptor tyrosine kinase inhibitor; and (ii) instructions stating that the IN10018 or a pharmaceutically acceptable salt thereof and the epidermal growth factor receptor tyrosine kinase inhibitor can be used to treat a tumor in a subject.

The compounds of the kit may be contained in separate containers. Alternatively, two or more compounds are contained in the same container. For example, the kit can comprise a first container, a second container, and a package insert, wherein the first container comprises at least one dose of a medicament comprising IN10018 or a pharmaceutically acceptable salt thereof, the second container comprises at least one dose of an epidermal growth factor receptor tyrosine kinase inhibitor, and the package insert comprises instructions for using the medicaments to treat tumors in an individual. The first and second containers may comprise the same or different shape (e.g., vials, syringes and bottles) and/or material (e.g., plastic or glass). The kit may further comprise other materials that are useful in administering the medicaments, such as diluents, filters, IV bags and lines, needles and syringes.

The precise amount of the IN10018 or a pharmaceutically acceptable salt thereof and the epidermal growth factor receptor tyrosine kinase inhibitor administered to a subject will depend on various factors, such as the given agent or compound, pharmaceutic preparation, route of administration, the type of disease, the condition, the identity of the subject or host being treated, etc., but can still be routinely determined by those skilled in the art. For example, determination of an effective amount will also depend on the degree, severity, and type of cell proliferation. The skilled artisan will be able to determine the appropriate dosage based on these and other factors.

IN10018 or a pharmaceutically acceptable salt thereof and the epidermal growth factor receptor tyrosine kinase inhibitor may be administered by suitable means such as oral, intravenous, intramuscular or subcutaneous administration.

For example, for oral administration, the drug may be administered orally with a pharmaceutically acceptable carrier such as an inert diluent or an absorbable edible carrier. They can be enclosed in hard- or soft-shell gelatin capsules, compressed into tablets, or mixed directly with the patient's food. For example, the drug can be in combination with one or more excipients and used in a form of ingestible tablets, buccal tablets, lozenges, capsules, elixirs, suspensions, syrups or wafers. Tablets, lozenges, pills, capsules, etc. may further comprise: binders such as tragacanth, acacia, cornstarch or gelatin; excipients such as dicalcium phosphate; disintegrants such as corn starch, potato starch, alginic acid, etc.; lubricants, such as magnesium stearate; or sweeteners, such as sucrose, fructose, lactose or aspartame; or flavoring agents.

For example, for infusion or injection by intravenous or intraperitoneal administration, a solution of the drug may be prepared in water, optionally mixed with a non-toxic surfactant.

Exemplary pharmaceutical dosage forms for injection or infusion include: sterile aqueous solutions, dispersions, or sterile powders containing the active ingredient suitable for the extemporaneous preparation of sterile injection or infusion solutions or dispersions. In any event, the final dosage form should be sterile, fluid, and stable under the conditions of manufacture and storage.

Sterile injection solutions can be prepared by incorporating a required amount of the drug and other desired ingredients enumerated above in an appropriate solvent and then being filtrated and sterilized. In the case of sterile powders for preparing sterile injection solutions, the preferred methods of preparation may be vacuum drying and the freeze-drying techniques, which yield a powder of the active ingredient plus any other desired ingredients present after previous sterile filtration.

The amount of the IN10018 or a pharmaceutically acceptable salt thereof and the epidermal growth factor receptor tyrosine kinase inhibitor may vary not only due to the particular agent chosen, but also due to the route of administration, the nature of the disease being treated, and the age and condition of the patient, and is ultimately at the discretion of the attending physician or clinician. However, the dosage may generally range from about 0.1 to about 50 mg/kg body weight per day.

In some embodiments, the IN10018 or a pharmaceutically acceptable salt thereof is administered at a dose of from 5 mg/day to 100 mg/day, e.g., 20 mg/day in an adult, as calculated on the basis of free base.

The epidermal growth factor receptor tyrosine kinase inhibitor is administered in a dose range of from 2 to 500 mg per day in an adult. In one specific embodiment, Osimertinib or a pharmaceutically acceptable salt thereof is administered in a dose range of 2-500 mg per day, e.g., 80 mg per day in an adult, as calculated on the basis of Osimertinib; Almonertinib or a pharmaceutically acceptable salt thereof is administered in a dose range of 2-250 mg per day, e.g., 110 mg per day in an adult, as calculated on the basis of Almonertinib; Alflutinib or a pharmaceutically acceptable salt thereof is administered in a dose range of 2-250 mg, e.g., 80 mg per day in an adult, as calculated on the basis of Alflutinib.

Technical and scientific terms used herein which are not specifically defined have the meanings commonly understood by the skilled artisan to which the invention belongs.

In some embodiments, the present disclosure also discloses the following:

1. Use of IN10018 or a pharmaceutically acceptable salt thereof and an epidermal growth factor receptor tyrosine kinase inhibitor in the manufacture of a medicament for the treatment of a tumor in a subject, the IN10018 having a structure of:

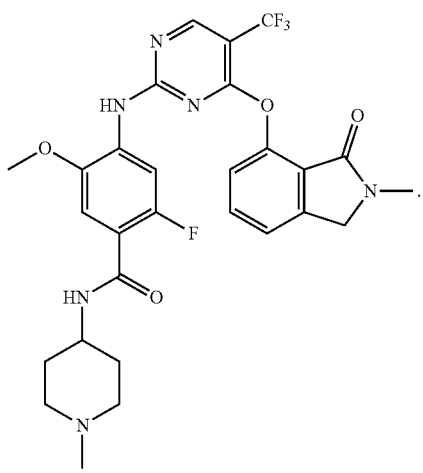

2. A pharmaceutical combination product of IN10018 or a pharmaceutically acceptable salt thereof and an epidermal growth factor receptor tyrosine kinase inhibitor, for use in the treatment of a tumor in a subject, the IN10018 having a structure of:

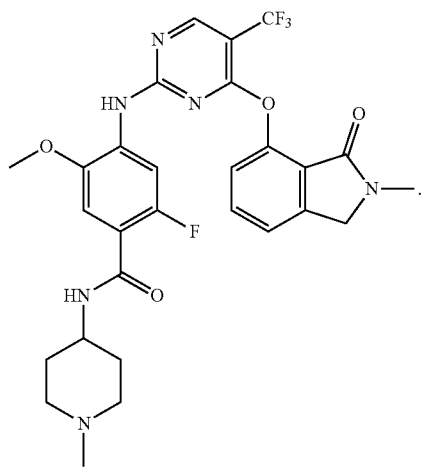

3. A method of treating a tumor, which comprises administering to a subject in need thereof a therapeutically effective amount of IN10018 or a pharmaceutically acceptable salt thereof and an epidermal growth factor receptor tyrosine kinase inhibitor, the IN10018 having a structure of:

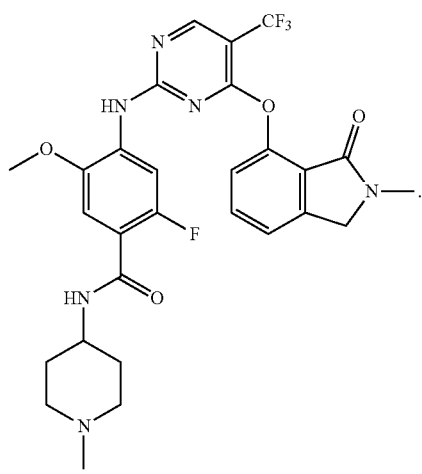

4. The use, pharmaceutical combination product, or method of any one of embodiments 1-3, wherein the pharmaceutically acceptable salt of the IN10018 is a tartrate salt.

5. The use, pharmaceutical combination product, or method of any one of embodiments 1-4, wherein the epidermal growth factor receptor tyrosine kinase inhibitor is Gefitinib, Erlotinib, Icotinib, Afatinib, Crizotinib, Osimertinib (AZD9291), Almonertinib, Alflutinib (also known as Furmonertinib), EAI045, JBJ-25-02, BLU945, BLU701, TQB3804, BBT-176, ES-072, BPI-361175, CH7233163, or a pharmaceutically acceptable salt thereof, alternatively Osimertinib, Almonertinib, Alflutinib, or a pharmaceutically acceptable salt thereof.

6. The use, pharmaceutical combination product, or method of any one of embodiments 1-5, wherein the IN10018 or a pharmaceutically acceptable salt thereof and the epidermal growth factor receptor tyrosine kinase inhibitor are administered simultaneously or sequentially to the subject.

7. The use, pharmaceutical combination product, or method of any one of embodiments 1-6, wherein the tumor is selected from bladder cancer, breast cancer, cervical cancer, colon cancer (including colorectal cancer), esophageal cancer, esophageal squamous cell carcinoma, head and neck cancer, liver cancer, lung cancer (including small cell lung cancer and non-small cell lung cancer), melanoma, myeloma, rhabdomyosarcoma, inflammatory myofibroblastic tumor, neuroblastoma, pancreatic cancer, prostate cancer, kidney cancer, renal cell carcinoma, sarcoma (including osteosarcoma), skin cancer (including squamous cell carcinoma), gastric cancer, testicular cancer, thyroid cancer, uterine cancer, mesothelioma, cholangiocarcinoma, leiomyosarcoma, liposarcoma, nasopharyngeal carcinoma, neuroendocrine carcinoma, ovarian cancer, salivary gland cancer, metastasis caused by spindle cell carcinoma, anaplastic large cell lymphoma, thyroid undifferentiated carcinoma, non-Hodgkin's lymphoma, Hodgkin's lymphoma, neuroglioma, and hematological malignancies, such as acute myeloid leukemia (AML), acute lymphoblastic leukemia (ALL), diffuse large B-cell lymphoma (DLBCL), follicular lymphoma (FL), chronic lymphocytic leukemia (CLL), or chronic myeloid leukemia (CML); alternatively, wherein the tumor is lung cancer, breast cancer, neuroglioma, esophageal cancer, head and neck cancer or colon cancer; alternatively, wherein the tumor is lung cancer or colon cancer.

8. A kit or pharmaceutically acceptable composition comprising:
(a) IN10018 or a pharmaceutically acceptable salt thereof; and
(b) an epidermal growth factor receptor tyrosine kinase inhibitor,
the IN10018 having a structure of:

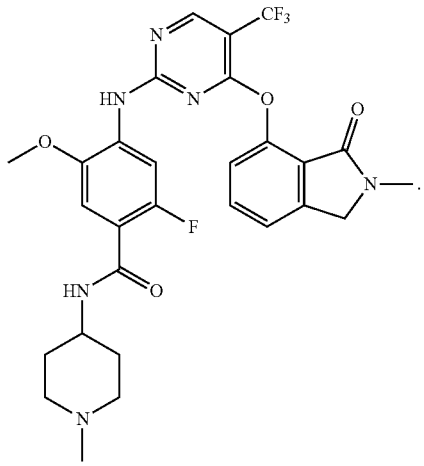

9. The kit or composition of embodiment 8, wherein the epidermal growth factor receptor tyrosine kinase inhibitor is Gefitinib, Erlotinib, Icotinib, Afatinib, Crizotinib, Osimertinib (AZD9291), Almonertinib, Alflutinib (also known as Furmonertinib), EAI045, JBJ-25-02, BLU945, BLU701, TQB3804, BBT-176, ES-072, BPI-361175, CH7233163, or a pharmaceutically acceptable salt thereof; alternatively Osimertinib, Almonertinib, Alflutinib, or a pharmaceutically acceptable salt thereof.

10. The kit or composition of any one of embodiments 8-9, which is used as a drug.

11. The kit or composition of any one of embodiments 8-10, wherein the pharmaceutically acceptable salt of the IN10018 is tartrate salt.

12. A method of treating a tumor in a subject, which comprises administering compounds in the kit or composition according to any of embodiments 8-11 to the subject simultaneously or sequentially.

13. The method of embodiment 12, the tumor is selected from bladder cancer, breast cancer, cervical cancer, colon cancer (including colorectal cancer), esophageal cancer, esophageal squamous cell carcinoma, head and neck cancer, liver cancer, lung cancer (including small cell lung cancer and non-small cell lung cancer), melanoma, myeloma, rhabdomyosarcoma, inflammatory myofibroblastic tumor, neuroblastoma, pancreatic cancer, prostate cancer, kidney cancer, renal cell carcinoma, sarcoma (including osteosarcoma), skin cancer (including squamous cell carcinoma), gastric cancer, testicular cancer, thyroid cancer, uterine cancer, mesothelioma, cholangiocarcinoma, leiomyosarcoma, liposarcoma, nasopharyngeal carcinoma, neuroendocrine carcinoma, ovarian cancer, salivary gland cancer, metastasis caused by spindle cell carcinoma, anaplastic large cell lymphoma, thyroid undifferentiated carcinoma, non-Hodgkin's lymphoma, Hodgkin's lymphoma, neuroglioma, and hematological malignancies, such as acute myeloid leukemia (AML), acute lymphoblastic leukemia (ALL), diffuse large B-cell lymphoma (DLBCL), follicular lymphoma (FL), chronic lymphocytic leukemia (CLL), and chronic myeloid leukemia (CML); alternatively, wherein the tumor is lung cancer, breast cancer, neuroglioma, esophageal cancer, head and neck cancer or colon cancer; alternatively, wherein the tumor is lung cancer or colon cancer.

14. A method of treating a tumor in a subject, which comprises administering to the subject a therapeutically effective amount of IN10018 or a pharmaceutically acceptable salt thereof and an epidermal growth factor receptor tyrosine kinase inhibitor; the IN10018 having a structure of:

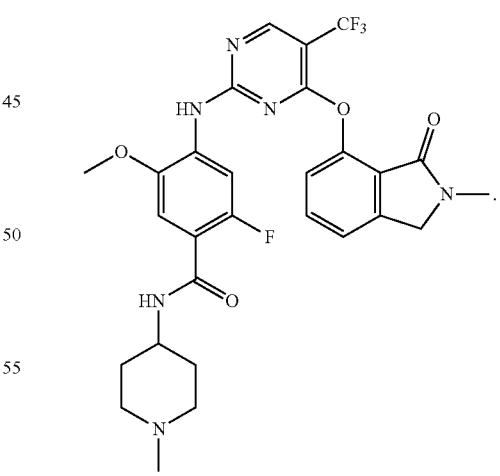

15. The method of embodiment 14, wherein the pharmaceutically acceptable salt of the IN10018 is the IN10018 tartrate salt.

16. The method of embodiment 14 or 15, wherein the epidermal growth factor receptor tyrosine kinase inhibitor is Gefitinib, Erlotinib, Icotinib, Afatinib, Crizotinib, Osimertinib (AZD9291), Almonertinib, Alflutinib (also known as Furmonertinib), EAI045, JBJ-25-02, BLU945, BLU701, TQB3804, BBT-176, ES-072, BPI-361175, CH7233163, or a pharmaceutically acceptable salt thereof; alternatively Osimertinib, Almonertinib, Alflutinib, or a pharmaceutically acceptable salt thereof.

17. The method of any one of embodiments 14-16, wherein the IN10018 or a pharmaceutically acceptable salt thereof and the epidermal growth factor receptor tyrosine kinase inhibitor are administered simultaneously or sequentially to the subject.

18. The method of any one of embodiments 14-17, wherein the tumor is bladder cancer, breast cancer, cervical cancer, colon cancer (including colorectal cancer), esophageal cancer, esophageal squamous cell carcinoma, head and neck cancer, liver cancer, lung cancer (including small cell lung cancer and non-small cell lung cancer), melanoma, myeloma, rhabdomyosarcoma, inflammatory myofibroblastic tumor, neuroblastoma, pancreatic cancer, prostate cancer, kidney cancer, renal cell carcinoma, sarcoma (including osteosarcoma), skin cancer (including squamous cell carcinoma), gastric cancer, testicular cancer, thyroid cancer, uterine cancer, mesothelioma, cholangiocarcinoma, leiomyosarcoma, liposarcoma, nasopharyngeal carcinoma, neuroendocrine carcinoma, ovarian cancer, salivary gland cancer, metastasis caused by spindle cell carcinoma, anaplastic large cell lymphoma, thyroid undifferentiated carcinoma, non-Hodgkin's lymphoma, Hodgkin's lymphoma, neuroglioma, or hematological malignancies, such as acute myeloid leukemia (AML), acute lymphoblastic leukemia (ALL), diffuse large B-cell lymphoma (DLBCL), follicular lymphoma (FL), chronic lymphocytic leukemia (CLL), or chronic myeloid leukemia (CML); alternatively, the tumor is lung cancer, breast cancer, neuroglioma, esophageal cancer, head and neck cancer, or colon cancer; alternatively, the tumor is lung cancer or colon cancer.

19. Use of IN10018 or a pharmaceutically acceptable salt thereof in the manufacture of a medicament for the treatment of a tumor in a subject, wherein the IN10018 or a pharmaceutically acceptable salt thereof and an epidermal growth factor receptor tyrosine kinase inhibitor are administered to the subject, the IN10018 having a structure of:

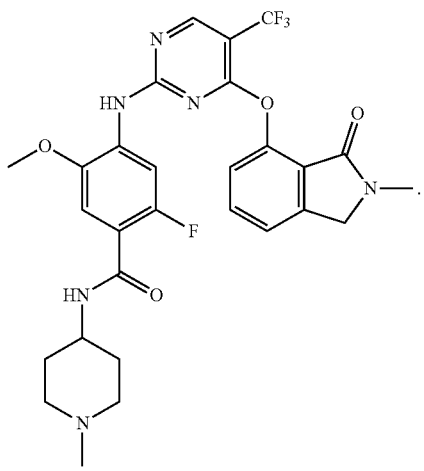

20. The use of embodiment 19, wherein the pharmaceutically acceptable salt of the IN10018 is the IN10018 tartrate salt.

21. The use of embodiment 19 or 20, wherein the epidermal growth factor receptor tyrosine kinase inhibitor is Gefitinib, Erlotinib, Icotinib, Afatinib, Crizotinib, Osimertinib (AZD9291), Almonertinib, Alflutinib (also known as Furmonertinib), EAI045, JBJ-25-02, BLU945, BLU701, TQB3804, BBT-176, ES-072, BPI-361175, CH7233163, or a pharmaceutically acceptable salt thereof; alternatively Osimertinib, Almonertinib, Alflutinib, or a pharmaceutically acceptable salt thereof.

22. The use of any one of embodiments 19-21, wherein the IN10018 or a pharmaceutically acceptable salt thereof and the epidermal growth factor receptor tyrosine kinase inhibitor are administered simultaneously or sequentially to the subject.

23. The use of any one of embodiments 19-22, wherein the tumor is bladder cancer, breast cancer, cervical cancer, colon cancer (including colorectal cancer), esophageal cancer, esophageal squamous cell carcinoma, head and neck cancer, liver cancer, lung cancer (including small cell lung cancer and non-small cell lung cancer), melanoma, myeloma, rhabdomyosarcoma, inflammatory myofibroblastic tumor, neuroblastoma, pancreatic cancer, prostate cancer, kidney cancer, renal cell carcinoma, sarcoma (including osteosarcoma), skin cancer (including squamous cell carcinoma), gastric cancer, testicular cancer, thyroid cancer, uterine cancer, mesothelioma, cholangiocarcinoma, leiomyosarcoma, liposarcoma, nasopharyngeal carcinoma, neuroendocrine carcinoma, ovarian cancer, salivary gland cancer, metastasis caused by spindle cell carcinoma, anaplastic large cell lymphoma, thyroid undifferentiated carcinoma, non-Hodgkin's lymphoma, Hodgkin's lymphoma, neuroglioma, or hematological malignancies, such as acute myeloid leukemia (AML), acute lymphoblastic leukemia (ALL), diffuse large B-cell lymphoma (DLBCL), follicular lymphoma (FL), chronic lymphocytic leukemia (CLL), or chronic myeloid leukemia (CML); alternatively, the tumor is lung cancer, breast cancer, neuroglioma, esophageal cancer, head and neck cancer or colorectal cancer; alternatively, the tumor is lung cancer or colorectal cancer.

24. Use of an epidermal growth factor receptor tyrosine kinase inhibitor in the manufacture of a medicament for the treatment of a tumor in a subject, wherein the epidermal growth factor receptor tyrosine kinase inhibitor and IN10018 or a pharmaceutically acceptable salt thereof are administered to the subject, the IN10018 having a structure of.

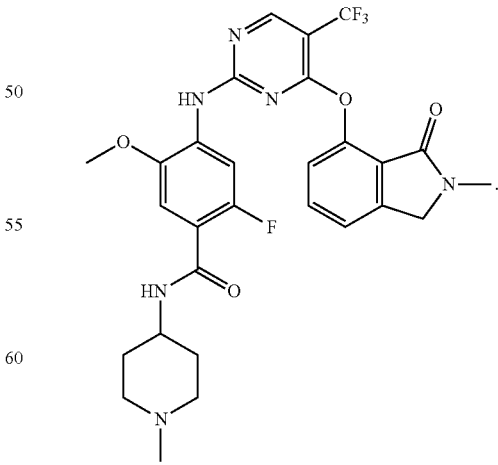

25. The use of embodiment 24, wherein the epidermal growth factor receptor tyrosine kinase inhibitor is Gefitinib, Erlotinib, Icotinib, Afatinib, Crizotinib, Osimertinib (AZD9291), Almonertinib, Alflutinib (also known as Furmonertinib), EAI045, JBJ-25-02, BLU945, BLU701, TQB3804, BBT-176, ES-072, BPI-361175, CH7233163, or a pharmaceutically acceptable salt thereof; alternatively Osimertinib, Almonertinib, Alflutinib, or a pharmaceutically acceptable salt thereof.

26. The use of embodiment 24 or 25, wherein the pharmaceutically acceptable salt of the IN10018 is the IN10018 tartrate salt.

27. The use of any one of embodiments 24-26, wherein the IN10018 or a pharmaceutically acceptable salt thereof and the epidermal growth factor receptor tyrosine kinase inhibitor are administered simultaneously or sequentially to the subject.

28. The use of any one of embodiments 24-27, wherein the tumor is bladder cancer, breast cancer, cervical cancer, colon cancer (including colorectal cancer), esophageal cancer, esophageal squamous cell carcinoma, head and neck cancer, liver cancer, lung cancer (including small cell lung cancer and non-small cell lung cancer), melanoma, myeloma, rhabdomyosarcoma, inflammatory myofibroblastic tumor, neuroblastoma, pancreatic cancer, prostate cancer, kidney cancer, renal cell carcinoma, sarcoma (including osteosarcoma), skin cancer (including squamous cell carcinoma), gastric cancer, testicular cancer, thyroid cancer, uterine cancer, mesothelioma, cholangiocarcinoma, leiomyosarcoma, liposarcoma, nasopharyngeal carcinoma, neuroendocrine carcinoma, ovarian cancer, salivary gland cancer, metastasis caused by spindle cell carcinoma, anaplastic large cell lymphoma, thyroid undifferentiated carcinoma, non-Hodgkin's lymphoma, Hodgkin's lymphoma, neuroglioma, or hematological malignancies, such as acute myeloid leukemia (AML), acute lymphoblastic leukemia (ALL), diffuse large B-cell lymphoma (DLBCL), follicular lymphoma (FL), chronic lymphocytic leukemia (CLL), or chronic myeloid leukemia (CML); alternatively, the tumor is lung cancer, breast cancer, neuroglioma, esophageal cancer, head and neck cancer or colon cancer; alternatively, the tumor is lung cancer or colon cancer.

29. Use of IN10018 or a pharmaceutically acceptable salt thereof and an epidermal growth factor receptor tyrosine kinase inhibitor in the manufacture of a medicament for the combined treatment of a tumor, the IN10018 having a structure of:

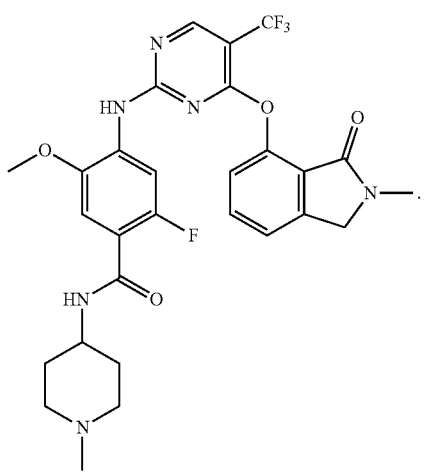

30. Use of IN10018 or a pharmaceutically acceptable salt thereof in the manufacture of a medicament for use in combination with an epidermal growth factor receptor tyrosine kinase inhibitor for the treatment of a tumor, the IN10018 having a structure of:

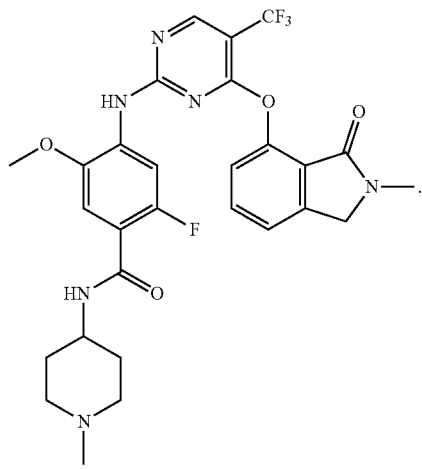

31. Use of an epidermal growth factor receptor tyrosine kinase inhibitor in the manufacture of a medicament for use in combination with IN10018 or a pharmaceutically acceptable salt thereof for the treatment of a tumor, the IN10018 having a structure of:

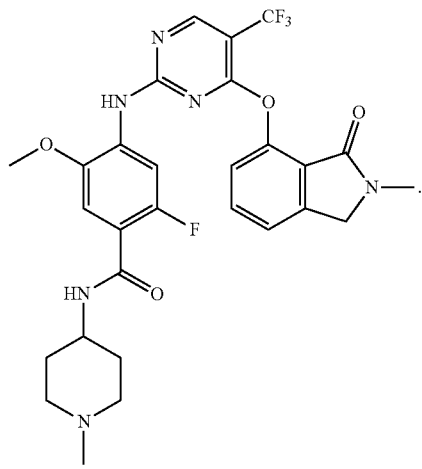

32. The use of any one of embodiments 29-31, wherein the IN10018 or a pharmaceutically acceptable salt thereof is the IN10018 tartrate salt.

33. The use of any one of embodiments 29-32, wherein the epidermal growth factor receptor tyrosine kinase inhibitor is Gefitinib, Erlotinib, Icotinib, Afatinib, Crizotinib, Osimertinib (AZD9291), Almonertinib, Alflutinib (also known as Furmonertinib), EAI045, JBJ-25-02, BLU945, BLU701, TQB3804, BBT-176, ES-072, BPI-361175, CH7233163, or a pharmaceutically acceptable salt thereof; alternatively Osimertinib, Almonertinib, Alflutinib, or a pharmaceutically acceptable salt thereof.

34. The use of any one of embodiments 29-33, wherein the IN10018 or a pharmaceutically acceptable salt thereof and the epidermal growth factor receptor tyrosine kinase inhibitor are administered simultaneously or sequentially to the subject.

35. The use of any one of embodiments 29-34, wherein the tumor is bladder cancer, breast cancer, cervical cancer, colon cancer (including colorectal cancer), esophageal cancer, esophageal squamous cell carcinoma, head and neck cancer, liver cancer, lung cancer (including small cell lung cancer and non-small cell lung cancer), melanoma, myeloma, rhabdomyosarcoma, inflammatory myofibroblastic tumor, neuroblastoma, pancreatic cancer, prostate cancer, kidney cancer, renal cell carcinoma, sarcoma (including osteosarcoma), skin cancer (including squamous cell carcinoma), gastric cancer, testicular cancer, thyroid cancer, uterine cancer, mesothelioma, cholangiocarcinoma, leiomyosarcoma, liposarcoma, nasopharyngeal carcinoma, neuroendocrine carcinoma, ovarian cancer, salivary gland cancer, metastasis caused by spindle cell carcinoma, anaplastic large cell lymphoma, thyroid undifferentiated carcinoma, non-Hodgkin's lymphoma, Hodgkin's lymphoma, neuroglioma, or hematological malignancies, such as acute myeloid leukemia (AML), acute lymphoblastic leukemia (ALL), diffuse large B-cell lymphoma (DLBCL), follicular lymphoma (FL), chronic lymphocytic leukemia (CLL), or chronic myeloid leukemia (CML); alternatively, the tumor is lung cancer, breast cancer, neuroglioma, esophageal cancer, head and neck cancer or colon cancer; alternatively, the tumor is lung cancer or colon cancer.

EXAMPLES

The following examples are provided to further illustrate the present disclosure. It should be understood that these examples are only used to illustrate the present disclosure and not to limit the scope of the present disclosure.

The experimental methods without specific conditions in the following examples can be carried out according to the conventional conditions of this type of reaction or according to the conditions suggested by the manufacturer.

The experimental materials and reagents used in the following examples can be obtained from commercial sources unless otherwise specified.

The meanings of the abbreviations used in the examples are as follows:

| Abbreviation | Name |
| --- | --- |
| DMSO | Dimethyl sulfoxide |
| SPF | Specific pathogen free |
| BW | Body weight |
| EDTA | Ethylene diamine tetraacetic acid |
| GLP | Good laboratory practice |
| p.o. | intragastric administration |
| annexin V | Annexin V |
| i.v. | Tail intravenous injection |
| Qd | Once a day |
| DPBS | Dulbecco's Phosphate-Buffered Saline |
| RT | Room temperature |
| SEM | Standard error of the mean |
| TGI | Tumor growth inhibition |
| TV | Tumor volume |
| TW | Tumor weight |
| FBS | Fetal bovine serum |
| PBS | Phosphate buffered Saline |
| $CO_2$ | Carbon dioxide |

Example 1: Study of IN10018 and AZD9291 in Lung Cancer KPL Cells

KPL cells (Institute of Cellular Sciences, CAS) were cultured with RPMI 1640 (Shanghai BasalMedia Technology Co., Ltd., Classification No.: L210KJ, Lot No.: F210916)+10% FBS (Gibco, Classification No.: 10099-141c, Lot No.: 2158737cp) and passaged twice. When the cells were in good condition, the culture was placed in a 24-well plate. Four groups were set up 24 hours after the cell plating. The first group was a negative control group with culture medium, the second group was IN10018 at 10 μM, the third group was AZD9291 at 10 μM, and the fourth group was a combination group with IN10018 (10 μM) and AZD9291 (10 μM). The drugs were mixed with cells and incubated in a 5% $CO_2$ incubator at 37° C. for 48 hours.

After 48 h of treatment with the drugs, cells were microscopically observed and photographed, and photographs were saved. Cells were then collected for flow analysis and washed twice with flow buffer (PBS+2% FBS). 0.5 μl of CoraLite®488 conjugated GRP94 polyclonal antibody (Proteintech, Classification No.: CL488-14700, Lot No.: 21006579) was added to each well, mixed, and incubated at 4° C. in dark for 20 min. After 20 min, the cells were washed twice with flow buffer (PBS+2% FBS). The cells were then analyzed on a flow cytometer.

The cells were observed under microscope. The AZD9291 single-drug group and the two-drug combination group had poor cell status, and the two-drug combination group was the worst with more cell death, while the negative control group and the IN10018 group had better cell status. See FIG. 1 and FIG. 2 for details.

Example 2: Study of IN10018 and Almonertinib in Lung Cancer KPL Cells

KPL cells (Institute of Cellular Sciences, CAS) were cultured with RPMI 1640 (Shanghai BasalMedia Technology Co., Ltd., Classification No.: L210KJ, Lot No.: F210916)+10% FBS (Gibco, Classification No.: 10099-141c, Lot No.: 2158737cp) and passaged twice. When the cells were in good condition, the culture was placed in a 24-well plate. Four groups were set up 24 hours after the cell plating. The first group was a negative control group with culture medium, the second group was IN10018 at 10 μM, the third group was Almonertinib at 4.7 μM, and the fourth group was a combination group with IN10018 (10 μM) and Almonertinib (4.7 μM). The drugs were mixed with cells and incubated in a 5% $CO_2$ incubator at 37° C. for 48 hours.

After 48 h of treatment with the drugs, cells were microscopically observed and photographed, and photographs were saved. Cells were then collected for flow analysis and washed twice with flow buffer (PBS+2% FBS). 0.5 μl of CoraLite®488 conjugated GRP94 polyclonal antibody (Proteintech, Classification No.: CL488-14700, Lot No.: 21006579) was added to each well, mixed, and incubated at 4° C. in dark for 20 min. After 20 min, the cells were washed twice with flow buffer (PBS+2% FBS). The cells were then analyzed on a flow cytometer.

Figure 4:
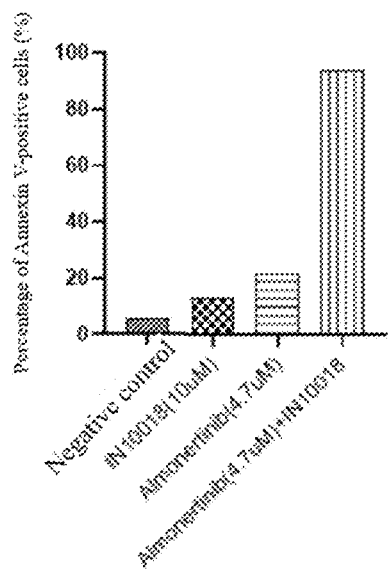
FIG. 4 shows the percentage of annexin V-positive KPL cells after incubation of Example 2 lung cancer KPL cells with the drug for 48 hours.

The cells were observed under microscope. The Almonertinib single-drug group and the two-drug combination group had poor cell status, and the two-drug combination group was the worst with more cell death, while the negative control group and the IN10018 group had better cell status. See FIG. 3 and FIG. 4 for details.

Example 3: Study of IN10018 and Alflutinib in Lung Cancer KPL Cells

KPL cells (Institute of Cellular Sciences, CAS) were cultured with RPMI 1640 (Shanghai BasalMedia Technology Co., Ltd., Classification No.: L210KJ, Lot No.:

F210916)+10% FBS (Gibco, Classification No.: 10099-141c, Lot No.: 2158737cp) and passaged twice. When the cells were in good condition, the culture was placed in a 24-well plate. Four groups were set up 24 hours after the cell plating. The first group was a negative control group with culture medium, the second group was IN10018 at 10 µM, the third group was Alflutinib at 4.7 µM, and the fourth group was a combination group with IN10018 (10 µM) and Alflutinib (4.7 µM). The drugs were mixed with cells and incubated in a 5% $CO_2$ incubator at 37° C. for 48 hours.

After 48 h of treatment with the drugs, cells were microscopically observed and photographed, and photographs were saved. Cells were then collected for flow analysis and washed twice with flow buffer (PBS+2% FBS). 0.5 µl of CoraLite®488 conjugated GRP94 polyclonal antibody (Proteintech, Classification No.: CL488-14700, Lot No.: 21006579) was added to each well, mixed, and incubated at 4° C. in dark for 20 min. After 20 min, the cells were washed twice with flow buffer (PBS+2% FBS). The cells were then analyzed on a flow cytometer.

Figure 5:
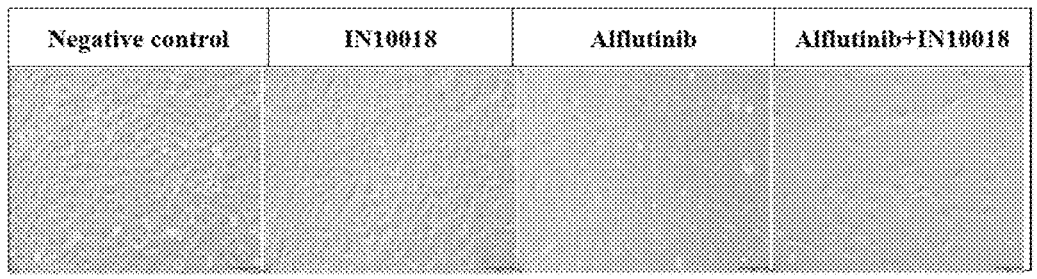
FIG. 5 shows white light micrographs of cells taken after incubation of Example 3 lung cancer KPL cells with the drug for 48 hours.
Figure 6:
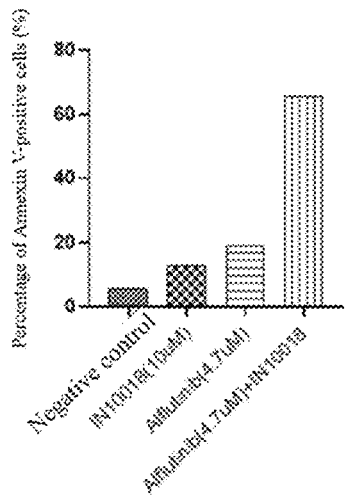
FIG. 6 shows the percentage of annexin V-positive KPL cells after incubation of Example 3 lung cancer KPL cells with the drug for 48 hours.

The cells were observed under microscope. The Alflutinib single-drug group and the two-drug combination group had poor cell status, and the two-drug combination group was the worst with more cell death, while the negative control group and the IN10018 group had better cell status. See FIG. 5 and FIG. 6 for details.

Example 4: In Vivo Antitumor Efficacy Study of AZD9291 in a Subcutaneous Allograft Tumor Model of Colon Cancer CT-26 Cells in BALB/c Mice Assay Material:

Mice: 6- to 8-week-old female BALB/c mice were purchased from Shanghai slack Laboratory Animal Co., Ltd. The animals arrived and were acclimatized in the assay environment before the assay was started. The animals were housed in IVC (Individual ventilation cage) in an SPF level animal room (5 animals per cage). All cages, litter and drinking water were sterilized prior to use. All laboratory personnel should wear protective clothing and latex gloves when operating in the animal room. Cages, forage and drinking water were changed twice a week. The housing environment and illumination conditions were as follows:

Temperature: 20-26° C.

Humidity: 40-70%

Illumination period: 12 hours of light and 12 hours of no light

Cage: made of polycarbonate, volume 300 mm×180 mm×150 mm. litter is corn cob, changed twice a week.

Food: Assay animals were free to eat (irradiated sterilized, dry pelleted food) throughout the experimental phase.

Drinking: Assay animals were free to drink sterilized water.

Cage identification: The animal information card for each cage indicated the quantity, sex, strain, date of receipt, dosing schedule, experiment number, group, and the start date of the assay for the animals in the cage.

Animal label: Assay animals were labeled by ear tags.

Compound information is shown in Table 1

TABLE 1

| | | | Compound information | | |
|---|---|---|---|---|---|
| Drug Name | Concentration (mg/mL) | Storage condition | Source | Vehicle | Total amount |
| AZD9291 | / | Normal temperature | Shanghai Superlan Chemcial Technology Centre | 5% DMSO + 40% PEG300 + 5% Tween-80 + 50% PBS | 130 mg |
| IN10018 | / | 4° C. | Synthesized according to the method in patent WO2010058032 | DPBS | 144 mg |
| Polyethylene glycol 300 (PEG300) | / | Normal temperature | SINOPHARM (30150728) | / | / |
| Dimethyl sulfoxide (DMSO) | / | Normal temperature | SIGMA (D2660) | / | / |
| Tween 80 (Tween-80) | / | Normal temperature | Aladdin (T104866) | / | / |

Colon cancer cells CT-26 (Source: Nanjing Cobioer Biosciences Co., Ltd., Stock No.: CBP60043) were maintained for passaging by Inxmed (Nanjing) Co., Ltd. Cells were cultured in monolayer in vitro in RPMI-1640 medium with 10% fetal bovine serum in a 37° C. 500 $CO_2$ incubator. The cells were passaged by routine digestion with trypsin-EDTA two to three times a week. When the cells were in the exponential growth phase with 80%-0% saturation, the cells were harvested, counted and inoculated.

Cell Inoculation and Grouping 0.1 mL of a cell suspension containing $3×10^5$ cells was inoculated subcutaneously into the right back of each mouse. When the tumor volume reached ~59 mm³ (on day 12 after cell inoculation), the mice were randomized into groups for administration according to the tumor volume, and the grouping information is shown in Table 2.

TABLE 2

Dosing regimen of test substances to CT-26 mouse transplantation tumor model

| Group | Compound therapy | Number of animal[1] | Dosage (mg/kg) | Administration volume parameter (mL/kg)[2] | Route of administration | Dosing frequency |
|---|---|---|---|---|---|---|
| 1 | Control group | 6 | N/A | 10 | p.o. | QD*16 days |
| 2 | IN10018 | 6 | 25 | 10 | p.o. | QD*16 days |
| 3 | AZD9291 | 6 | 20 | 10 | p.o. | QD*16 days |
| 4 | AZD9291 + IN10018 | 6 | 20 + 25 | 10 | p.o. + p.o.. | QD*16 days + QD*16 days |

Note:
[1] Number of mice per group;
[2] Administration volume: 10 mL/kg according to the body weight of the mice. If the body weight decreases more than 15%, the administration to the animal was stopped; the administration was resumed until the body weight recovered to 10% lower.

Preparation of the Test Substances
See Table 3 for details

TABLE 3

Preparation of the test substances

| Drug Name | Dosage (mg/kg) | Concentration (mg/mL) | Formulation process |
|---|---|---|---|
| Control group (5% DMSO + 40% PEG300 + 5% Tween-80 + 50% PBS) | / | / | 1.5 ml DMSO, 12 ml PEG300, 1.5 ml Tween-80 and 15 ml PBS were pipetted in turn, and the mixture was vortexed. |
| AZD9291 | 20 | 2 | 130 mg of AZD9291 powder was weighed, and 3.25 ml of DMSO was added. The mixture was mixed by ultrasonic vortex to prepare the stock solution. For each use, 0.75 ml of the stock solution was aspirated, and 6 ml of PEG300, 0.75 ml of Tween-80 and 7.5 ml of PBS were added in turn, and the mixture was vortexed ultrasonically to make a clarified solution. Preparation was conducted once every 4 days |
| IN10018 | 25 | 2.5 | 36 mg of the IN10018 tartrate was weighed, diluted with 14.4 mL of DPBS. The mixture was mixed thoroughly to make a clarified solution. Preparation was conducted once every 4 days |

Daily Observation of Assay Animals

Animals were monitored daily for health and death. Routine examinations included observation of tumor growth and the effects of drug treatment on the animals' daily behavior such as behavioral activities, food and water intake (visual inspection only), weight changes, appearance signs or other abnormalities. Animal deaths and side effects in each group were recorded based on the number of animals in each group.

Assay Termination

If the animal's health condition continued to deteriorate, or the tumor volume exceeded 3,000 mm$^3$, or the animal had serious illness or pain, the animal needed to be euthanized. Veterinarians were notified and the animal was euthanized in the following circumstances: being thin significantly, and the weight loss being greater than 20%; being unable to freely feed and drink; the average tumor volume in the control group reached 2,000 mm$^3$ and the experiment was terminated. Animals exhibited the following clinical manifestations and continued to deteriorate: piloerection, arched back, pale ear, nose, eye or foot, breathing hastily, convulsion, continuous diarrhea, dehydration, slow movement, or sound.

Tumor Measurements and Assay Indicators

The tumor diameter was measured with a vernier caliper three times a week. The tumor volume was calculated by the formula: $V=0.5 \times a \times b^2$, where a and b indicated the long and short diameter of the tumor, respectively.

The tumor growth inhibition rate TGI (%) was calculated with reference to the tumor volume on the first day after grouping according to the following formula:

TGI (%)=[1−(mean tumor volume of a dosing group−mean tumor volume at the start of treatment for that dosing group)/(mean tumor volume of the vehicle control group−mean tumor volume at the start of treatment for the vehicle control group)]×100%.

Statistical Analysis

Statistical analysis was performed based on tumor volume and tumor weight at the end of the trial using Prism Graphpad software. Comparisons among multiple groups were analyzed using Two-way ANOVA, Fisher's LSD test method. P<0.05 was considered a significant difference.

Results of the Assay

In vivo efficacy of the test substance AZD9291 in combination with IN10018 in a BALB/c mouse subcutaneous allograft tumor model of CT-26 mouse colon cancer cell.

After cell inoculation, tumor growth was observed daily. Grouping was based on tumor volume on day 11 after inoculation, and the average tumor volume when they were enrolled into the groups was approximately 38 mm³. Due to tumor bearing, the control group was euthanized on day 26 after inoculation, i.e., day 15 after administration by groups, and the entire assay was stopped.

Figure 7:
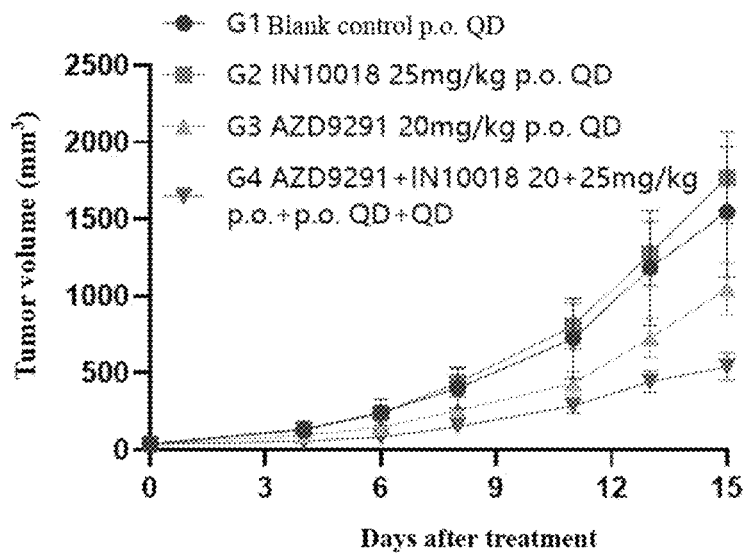
FIG. 7 shows the changes in tumor growth in the BALB/c mouse allograft tumor model of mice colon cancer CT-26 in Example 4 after administration of different test substances to the tumor-bearing mice.

On day 15 after administration by groups, the tumor volume in the control group was 1546.6±1038.8 mm³. The tumor volume in individual treatment group was 1766.9±732.5 mm³, 1046.3±407.8 mm³ and 540.4±218.0 mm³ for IN10018 (25 mg/kg), AZD9291 (20 mg/kg) and AZD9291+IN10018 (20+25 mg/kg), respectively, as detailed in Table 4. When the tumor volumes were compared with that of the control group, the tumor growth inhibition rates TGI were −14.5% (p=0.3079), 33.2% (p=0.0216) and 66.6% (p<0.0001) for IN10018 (25 mg/kg), AZD9291 (20 mg/kg) and AZD9291+IN10018 (20+25 mg/kg) groups, respectively. Details are shown in Table 4. The tumor volumes were compared with that of the AZD9291+IN10018 (20+25 mg/kg) combination group and statistically analyzed to show p values of p<0.0001, p<0.0001 and p=0.0202 for the control group, the IN10018 (25 mpk) single-drug group, and the AZD9291 (20 mpk) single-drug group, respectively. Tumor volumes for each dose group at different time periods are shown in FIG. 7.

TABLE 4

Evaluation of tumor suppressive effect of the test substances on BALB/c mouse transplantation tumor model of mouse colon cancer CT-26 cells (Based on data on day 15 after administration by groups)

| Group | Tumor volume on day 0 (mm³)[1] | Tumor volume on day 15 (mm³) | TGI (%) | P value[2] | P value[3] |
|---|---|---|---|---|---|
| Control group | 37.9 ± 15.6 | 1546.6 ± 1038.8 | / | / | <0.0001**** |
| IN10018 | 39.2 ± 17.9 | 1766.9 ± 732.5 | −14.5 | 0.3079 | <0.0001**** |
| AZD9291 | 37.9 ± 12.9 | 1046.3 ± 407.8 | 33.2 | 0.0216* | 0.0202* |
| AZD9291 + IN10018 | 37.0 ± 9.34 | 540.4 ± 218.0 | 66.6 | <0.0001**** | / |

Note:
[1]Calculated according to the number of days after administration by groups and the data were the mean ± standard error.
[2]*: $p < 0.05$, ****: $p < 0.0001$, vs. the control group, Two-way ANOVA.
[3]*: $p < 0.05$, ****: $p < 0.0001$, vs. AZD9291 + IN10018 (20 + 25 mg/kg) group, Two-way ANOVA.

Figure 8:
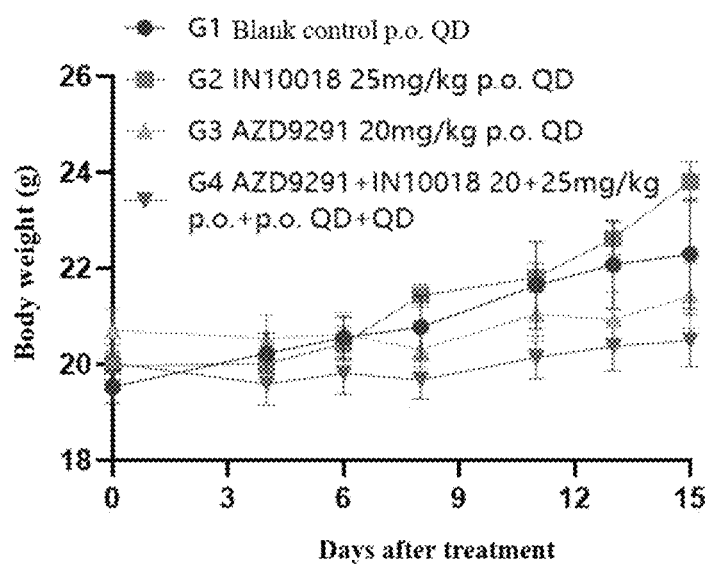
FIG. 8 shows the change in body weight of CT-26 tumor-bearing mice after administration of different test substances in Example 4.

The assay was carried out according to the dosing regimen, during which the animals were observed daily for feeding and drinking, and their body weights were recorded three times a week. Their body weight curves are shown in FIG. 8. During the whole dosing cycle, the animals in all groups showed no significant weight loss and were in good condition.

Conclusion

Compared with the blank control group, both AZD9291 (20 mg/kg) and AZD9291+IN10018 (20+25 mg/kg) groups showed obvious tumor growth inhibition with statistical difference from the control group. Generally, throughout the dosing cycle, the AZD9291+IN10018 (20+25 mg/kg) group consistently had smaller tumor volume than the IN10018 (25 mg/kg) group and the AZD9291 (20 mg/kg) group with statistical significance compared to both groups, and had better tumor growth inhibition relative to the IN10018 (25 mg/kg) group and the AZD9291 (20 mg/kg) group. At the same time, the animals showed good changes in body weight and no abnormalities in activity, water intake and mental status throughout the dosing cycle, indicating that the animals tolerated the combination of AZD9291+IN10018 (20+25 mg/kg).

Example 5: In Vivo Antitumor Efficacy Study of AZD9291 and IN10018 in BALB/c-Nude Mouse Subcutaneous Xenograft Tumor Model of Human Non-Small Cell Lung Cancer HCC827 Cells

| Assay material | |
|---|---|
| Strain | BALB/c-nude mice |
| Body weight/week of age | 5-6 weeks old |
| Sex | Female |
| Number | 54 mice (including the remaining mice after grouping) |
| Supplier | Vital River |
| Assay facilities | SPF level animal room from Nangjing ClinBridge Biotech Co., Ltd. |

-continued

| | Assay material |
|---|---|
| Animal quarantine | The animals were acclimatized in the experimental environment for at least 3 days after arrival before starting the assay |
| Temperature | 20-26° C. |
| Humidity | 40-70% |
| Illumination cycle | 12 hours of light, 12 hours of no light |
| Cage Information | Made of polycarbonate, volume 300 mm × 180 mm × 150 mm. litter is corn cob, changed twice a week. All cages and litter need to be sterilized before use. |
| Cage Identification | The animal information card for each cage indicated the quantity, sex, strain, date of receipt, dosing schedule, experiment number, group, and the start date of the assay for the animals in the cage. |
| Food and drinking | Assay animals were free to eat (irradiated sterilized, dry pelleted food) throughout the experimental phase. |
| Feeding density | 5 mice/cage |
| Animal label | Assay animals were labeled by ear tags. |

| Name | AZD9291 | IN10018 |
|---|---|---|
| Supplier | Shanghai Superlan Chemcial Technology Centre | Synthesized according to the method in patent WO2010058032 |
| Lot No./Stock No. | Lot: 202012-02 | Lot: CR-C18091729-B19001 |
| Characteristic | Yellow powder | White powder |
| Vehicle | 5% DMSO + 40% PEG300 + 5% Tween-80 + 50%PBS | DPBS |
| Storage conditions | | Normal temperature |
| Amount of current use | 42.75 mg | 618.75 mg |

| Name | Code Name | Source | Storage condition |
|---|---|---|---|
| Polyethylene glycol 300 | PEG300 | SINOPHARM (30150728) | Normal temperature |
| Dimethyl sulfoxide | DMSO | SIGMA (D2660) | Normal temperature |
| Tween 80 | Tween-80 | Aladdin (T104866) | Normal temperature |
| Dulbecco's phosphate buffer | DPBS | Shanghai BasalMedia (B210KJ) | 4° C. |

| Name | Dosage (mg/kg) | Concentration (mg/ml) | Formulation process | Storage conditions and preparation frequency |
|---|---|---|---|---|
| Control group | N/A | N/A | 1.5 ml DMSO, 12 ml PEG300, 1.5 ml Tween-80 and 15 ml PBS were pipetted in turn, and the mixture was vortexed. | Stored at 4° C. |
| AZD9291 | 3 | 0.3 | 33.3 mg of AZD9291 powder was weighed, and 5.55 ml of DMSO was added. The mixture was vortexed ultrasonically to prepare the stock solution. For each use, 0.6 ml of the stock solution was aspirated, and 4.8 ml of PEG300, 0.6 ml of Tween-80 and 6.0 ml of PBS were added in turn, and the mixture was vortexed ultrasonically to make a clarified solution. | Stored at 4° C., and preparation was conducted once every 4 days |
| IN10018 | 25 | 2.5 | 75 mg of the IN10018 was weighed, and diluted with 30.0 mL of DPBS. The mixture was vortexed thoroughly to make a clarified solution. | Stored at 4° C., and preparation was conducted once every 4 days. |

Assay Methods and Procedures

Human non-small cell lung cancer cells HCC827 (Source: Shanghai Cell Bank, Stock No.: TCHu153) were maintained for passaging by Nangjing ClinBridge Biotech Co., Ltd. Cells were cultured in monolayer in vitro in RPMI-1640 medium+10% FBS in a 37° C. 5% $CO_2$ incubator. The cells were passaged by routine digestion with trypsin-EDTA two to three times a week. When the cells were in the exponential growth phase with 80%-90% saturation, the cells were harvested, counted and inoculated. 0.1 mL of a cell suspension containing $5 \times 10^6$ cells was inoculated subcutaneously into the right back of each mouse. When the tumor volume reached about 147 mm³ (on day 16 after cell inoculation), the mice were randomized into groups for administration according to the tumor volume, and the grouping information is shown in Table 5.

TABLE 5

Animal groups and dosing regimen of drug efficacy assay in vivo

| Group | N[1] | Test drug | Dosage (mg/kg) | Administration volume parameter (mL/kg) [2] | Route of administration | Dosing frequency |
|---|---|---|---|---|---|---|
| 1 | 5 | Control group | N/A | 10 | PO | QD × 32 |
| 2 | 5 | IN10018 | 25 | 10 | PO | QD × 37 |
| 3 | 5 | AZD9291 | 3 | 10 | PO | QD × 37 |
| 4 | 5 | AZD9291 + IN10018 | 3 + 25 | 10 + 10 | PO + PO | QD × 37 + QD × 37 |

Note:
[1] N represents number of mice per group;
[2] Administration volume was 10 mL/kg according to the body weight of the mice. If the body weight decreases more than 15%, the administration to the animal was stopped; the administration was resumed until the body weight recovered to 10% lower.

Daily Observation of Assay Animals

The use and welfare of laboratory animals were in accordance with the AAALAC regulations. Animals were monitored daily for health and death. Routine examinations included observation of tumor growth and the effects of drug treatment on the animals' daily behavior such as behavioral activities, food and water intake (visual inspection only), weight changes, appearance signs or other abnormalities. Animal deaths and side effects in each group were recorded based on the number of animals in each group.

Assay Termination

If the animal's health condition continued to deteriorate, or the tumor volume exceeded 3,000 mm$^3$, or the animal had serious illness or pain, the animal needed to be euthanized. Veterinarians were notified and the animal was euthanized in the following circumstances: being thin significantly, and the weight loss being greater than 20%; being unable to freely feed and drink; the average tumor volume in the control group reached 2,000 mm$^3$ and the experiment was terminated. Animals exhibited the following clinical manifestations and continued to deteriorate: piloerection, arched back, pale ear, nose, eye or foot, breathing hastily, convulsion, continuous diarrhea, dehydration, slow movement, or sound.

Tumor Measurements and Assay Indicators

The experiment criteria was to investigate whether the tumor growth was inhibited, delayed or cured. Tumor diameter was measured three times a week using vernier calipers. Tumor volume was calculated according to the following formula: V=0.5×a×b$^2$, where a and b indicated the long diameter and short diameter of the tumor, respectively.

The tumor suppressive efficacy of the compounds was evaluated by TGI (%), which reflects the tumor growth inhibition rate. The tumor growth inhibition rate TGI (%) was calculated with reference to the tumor volume on the first day after grouping according to the following formula:

TGI (%)=[1−(mean tumor volume of a dosing group−mean tumor volume at the start of treatment for that dosing group)/(mean tumor volume of the vehicle control group−mean tumor volume at the start of treatment for the vehicle control group)]×100%.

Statistical Analysis

Statistical analysis was performed based on tumor volume at the end of the trial using Prism Graphpad software. Comparisons among multiple groups were analyzed using Two-way ANOVA, Fisher's LSD test method, and P<0.05 was considered a significant difference. Comparisons between the two groups were analyzed using the t-test, Mann Whitney test method test, and P<0.05 was considered a significant difference.

Results of the Assay

After cell inoculation, tumor growth was observed daily. Grouping was based on to tumor volume on day 16 after inoculation, and the average tumor volume when they were enrolled into the groups was approximately 147 mm$^3$. Due to tumor bearing, the control group was euthanized on day 48 after inoculation, i.e., day 32 after administration by groups. The AZD9291 high dose (3 mg/kg) group and the combination group associated with the IN10018 25 mg/kg were euthanized on day 53 after inoculation, i.e. day 37 after administration by group, and the entire assay was stopped.

Figure 9:
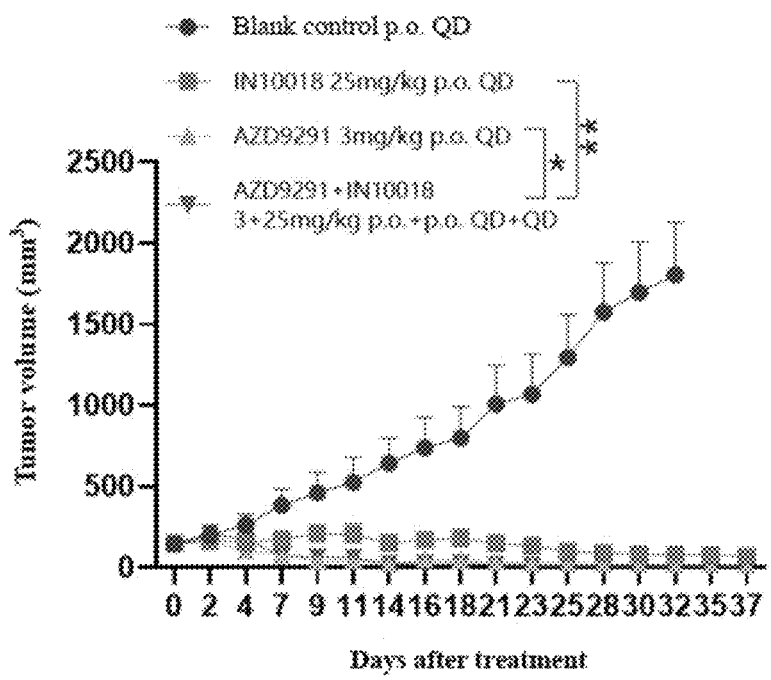
FIG. 9 shows the tumor growth curve of mice after administration of different test substances in Example 5, with data points representing the mean tumor volume within the group and error lines representing standard error of the mean (SEM).

On day 32 after administration by groups, the tumor volume in the control group was 1805.6±722.8 mm$^3$. The tumor volume in each treatment group was 20.3±4.7 mm$^3$, 79.2±51.8 mm$^3$ and 9.0±7.0 mm$^3$ for AZD9291 (3 mg/kg), IN10018 (25 mg/kg) and AZD9291+IN10018 (3+25 mg/kg), respectively. When the tumor volumes were compared with that of the control group, the tumor growth inhibition rates TGI were 107.7% (p<0.0001), 104.1% (p<0.0001) and 108.4% (p<0.0001) for AZD9291 (3 mg/kg), IN10018 (25 mg/kg) and AZD9291+IN10018 (3+25 mg/kg) groups, respectively. Details are shown in Table 5-1. The tumor volumes of each dose group at different time periods are shown in FIG. 9.

Figure 10:
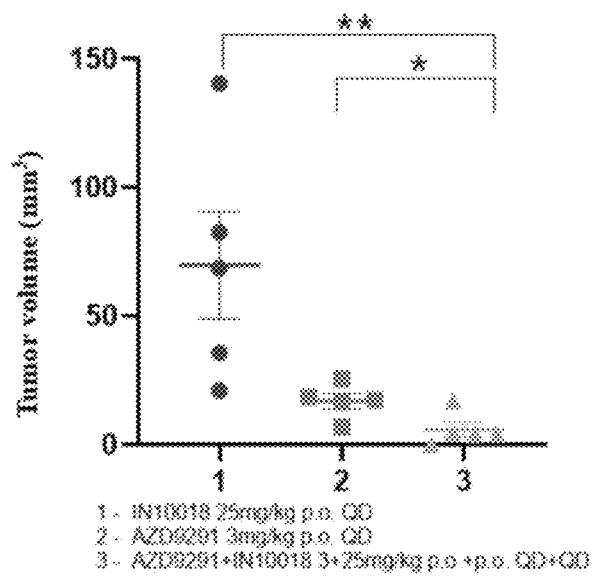
FIG. 10 shows tumor data for each treatment group at the experimental endpoint in Example 5, with data points representing tumor volume per animal within the group and error lines representing standard error of the mean (SEM).

On day 32 after administration by groups, the control group was euthanized for excessive tumor volume, and the AZD9291 (3 mg/kg), IN10018 (25 mg/kg) and AZD9291+IN10018 (3+25 mg/kg) groups continued dosing and observation until day 37. On day 37 after administration by groups, the tumor volumes in the AZD9291 (3 mg/kg) group and the IN10018 (25 mg/kg) group were 17.0±6.7 mm$^3$ and 69.6±46.6 mm$^3$, respectively. The tumor volume in the AZD9291+IN10018 (3+25 mg/kg) two-drug combination group was 5.8±6.5 mm$^3$. When the tumor volumes were compared with that of the AZD9291+IN10018 (3+25 mg/kg) two-drug combination group, the p-values were p=0.0317 and p=0.0079 for the AZD9291 (3 mg/kg) group and the IN10018 (25 mg/kg) group, respectively, both of which were statistically significant. The details are shown in Table 5-2. The tumor volumes of each dose group at different time periods are shown in FIG. 9. The tumor volumes of each dose group at the end of the assay are shown in FIG. 10.

TABLE 5-1

Evaluation of tumor suppressive effect of the test substances on BALB/c-nude mouse transplantation tumor model of human non-small cell lung cancer HCC827 cells (based on data on day 32 after administration by groups)

| Group | Tumor volume on day 0 (mm³)[1] | Tumor volume on day 32 (mm³)[1] | TGI (%) | P value[2] |
|---|---|---|---|---|
| Control group | 147.6 ± 53.5 | 1805.6 ± 722.8 | / | / |
| AZD9291 3 mpk | 148.6 ± 59.6 | 20.3 ± 4.7 | 107.7 | <0.0001 **** |
| IN10018 25 mpk | 147.7 ± 56.3 | 79.2 ± 51.8 | 104.1 | <0.0001 **** |
| AZD9291 + IN10018 3 + 25 mpk | 147.6 ± 61.3 | 9.0 ± 7.0 | 108.4 | <0.0001 **** |

Note:
[1] Calculated according to the number of days after administration by groups and the data are the mean + standard deviation (mean + SD);
[2] ****: $p < 0.0001$, vs. the control group, Two-way ANOVA.

TABLE 5-2

Evaluation of tumor suppressive effect of the test substances on BALB/c-nude mouse transplantation tumor model of human non-small cell lung cancer HCC827 cells (based on data on day 37 after administration by groups)

| Group | Tumor volume on day 0 (mm³)[1] | Tumor volume on day 37 (mm³)[1] | P value[2] |
|---|---|---|---|
| AZD9291 3 mpk | 148.6 ± 59.6 | 17.0 ± 6.7 | 0.0317 * |
| IN10018 25 mpk | 147.7 ± 56.3 | 69.6 ± 46.6 | 0.0079 ** |
| AZD9291 + IN10018 3 + 25mpk | 147.6 ± 61.3 | 5.8 ± 6.5 | / |

Note:
[1] calculated according to the number of days after administration by groups and the data are the mean ± standard deviation (mean ± SD);
[2] *: $p < 0.05$, **: $p < 0.01$, vs. AZD9291 + IN10018 (3 + 25 mg/kg), t-test, Mann Whitney test.

The assay was carried out according to the dosing regimen, during which the animals were observed daily for feeding and drinking, and their body weights were recorded three times a week. After 28 days of administration by groups, the mean body weight of the control group changed from 20.0 g on the day of administration by groups (Day 0) to 19.4 g, with a weight growth rate of −3.3%; the mean body weight of the IN10018 (25 mg/kg) treatment group changed from 21.3 g on Day 0 to 20.7 g on Day 28 with a weight change rate of −2.6%.

After 37 days of administration by groups, the mean body weight in the AZD9291 (3 mg/kg) group and the IN10018 (25 mg/kg) group changed from 19.9 g and 21.3 g on Day 0 to 19.4 g and 20.3 g on Day 37, with a weight change rate of −2.2% and −4.5%, respectively; the mean body weight in the AZD9291+IN10018 (3+25 mg/kg) group changed from 20.0 g on Day 0 to 19.5 g on Day 37, with a weight change rate of −2.3%.

Figure 11:
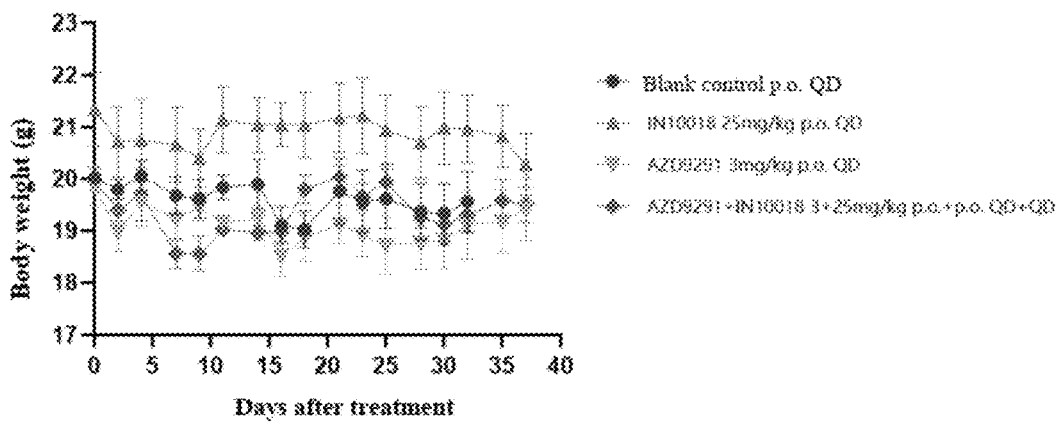
FIG. 11 shows the change in body weight of mice after administration of different test substances in Example 5, with data points representing the mean body weight within the group and error lines representing standard error of the mean (SEM).

The animals in all groups showed no significant weight loss and were in good condition throughout the dosing cycle. The details are shown in Table 5-3. The changes in body weight at different time periods for the relevant groups of AZD9291 (3 mg/kg) and IN10018 are shown in FIG. 11.

TABLE 5-3

Evaluation of body weight changes of the BALB/c-nude mouse transplant tumor model of human non-small cell lung cancer HCC827 cells by the test substances (based on data on day 28/37 after administration by groups)

| Group | Animal Survival[1] | Body weight on day 0 (g)[2] | Body weight on day 28 (g)[2] | Body weight on day 37 (g)[2] | Rate of change in body weight (%)[3] |
|---|---|---|---|---|---|
| Control group | 5/5 | 20.0 ± 0.2 | 19.4 ± 1.2 | | −3.3 |
| IN10018 25 mg/kg | 5/5 | 21.3 ± 1.6 | 20.7 ± 1.6 | | −2.6 |
| AZD9291 3 mg/kg | 5/5 | 19.9 ± 0.9 | | 19.4 ± 1.4 | −2.2 |
| AZD9291 + IN10018 3 + 25 mg/kg | 5/5 | 20.0 ± 0.5 | | 19.5 ± 0.8 | −2.3 |

Note:
[1] Number of animals surviving on day 0/Number of animals surviving on day 15 after administration by groups;
[2] Data are mean ± standard deviation (mean ± SD);
[3] Rate of change in body weight = $[1 - (W_t - W_0)/W_0]*100\%$.

Conclusion

Compared with the blank control group, each of AZD9291 (3 mg/kg), IN10018 (25 mg/kg), and AZD9291+ IN10018 (3+25 mg/kg) groups showed obvious tumor growth inhibition with statistical difference from the control group. Throughout the dosing cycle, the AZD9291+ IN10018 (3+25 mg/kg) group had consistently smaller tumor volume than the AZD9291 (3 mg/kg) group and the IN10018 (25 mg/kg) group with statistical difference from both single-drug groups, which shown that the two-drug combination of AZD9291+IN10018 (3+25 mg/kg) had better inhibition on tumor growth.

Example 6: Synergistic Tumor-Killing Effects Produced by the Combination of IN10018 and AZD-9291

In vitro assay the killing curve of AZD9291 in lung cancer cells HCC827 was detected and the IC50 value was determined. The cytotoxic effect of AZD-9291 at different doses in combination with 3 µM IN10018 and 5 µM IN10018 respectively was explored. The cell apoptotic response to single drug and drug combination was also detected using flow cytometry with Annexin V staining.

Assay antibodies: recombinant Alexa Fluor® 647 fluorescent Anti-Calreticulin antibody (Abcam, ab196159), FAK antibody (CST, 3285S), Phospho-eIF2α (Ser51) (CST, 3398), eif2α (CST, 5324), DDIT3 (HUABIO, ET1703-05), HRP-tagged Alpha tubulin (α-microtubulin) antibody (Proteintech, HRP-66031).

1. Synergistic Tumor-Killing Effects Produced by the Combination of IN10018 and AZD-9291

Figure 12:
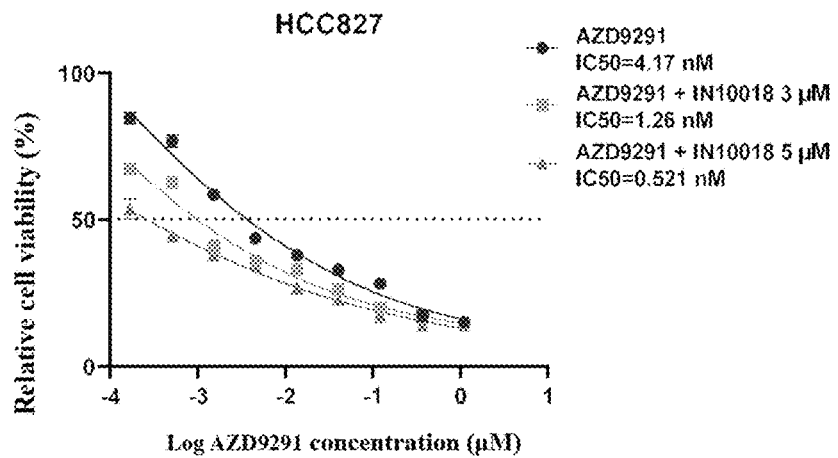
FIG. 12 shows the killing synergistic effect of AZD9291 at different doses in combination with 3 μM IN10018 and 5 μM IN10018 for 48 h on non-small cell lung cancer cells HCC827 in Example 6.

5000 HCC827 cells/well were plated in a 96-well plate, and 24 hours later, a fixed concentration of the IN10018 was added in combination with different concentrations of AZD9291. The concentrations of the IN10018 were 3 µM and 5 µM; and a total of 9 concentrations of AZD9291 were prepared by 3-fold serial dilution of the maximum concentration of 1 µM. After co-incubation of the drug and cells for 72 hours, 10 µL of CCK8 solution was added to each well and incubated at 37° C. in a 5% $CO_2$ incubator for 2 hours, and a microplate reader with an absorbance wavelength of 450 nm was used. The readings were compared with the DMSO control group and plotted using Graphpad 8.0. See FIG. 12 for details.

2. Apoptosis Promoted by the Combination of IN10018 and AZD-9291

Figure 13:
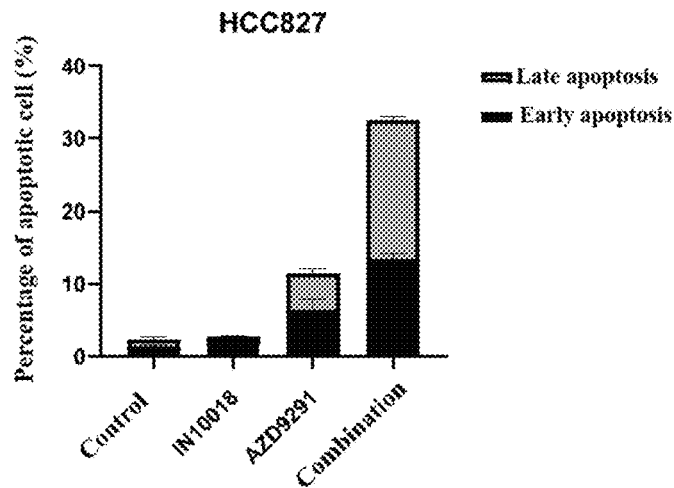
FIG. 13 shows the detection of apoptosis after treatment of HCC827 cells with 0.3 nM AZD9291 in combination with 3 μM IN10018 for 48 hours in Example 6.

HCC827 cells were treated with 0.3 nM AZD9291 in combination with 3 µM IN10018. Cells were collected after 48 h for cell staining using Annexin V kit, and were detected using flow cytometry. Early and late apoptotic cell values were counted for comparison with the DMSO control group, and plotted using Graphpad 8.0. See FIG. 13 for details. The results showed that early and late apoptosis were significantly enhanced in the combination group compared to the single-drug groups.

All references mentioned herein are incorporated by reference in their entirety, as if each were individually listed. It should be understood that after reading the disclosure of the present invention, those skilled in the art can make various changes or modifications to the present invention, and these equivalent forms also fall within the scope defined by the appended claims of the present application.

What is claimed is:

1. A method of treating a tumor, which comprises administering to a subject in need thereof a therapeutically effective amount of IN10018 or a pharmaceutically acceptable salt thereof and an epidermal growth factor receptor tyrosine kinase inhibitor, wherein the IN10018 has a structure of:

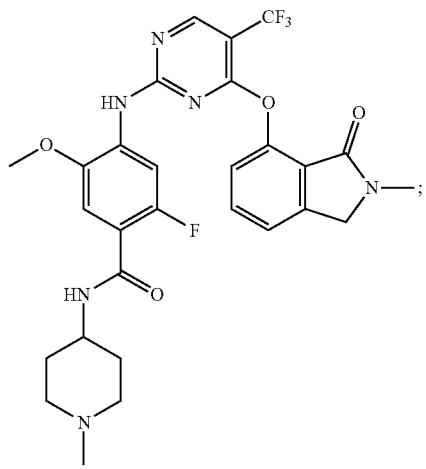

and
the epidermal growth factor receptor tyrosine kinase inhibitor is selected from the group consisting of Icotinib, Afatinib, Crizotinib, Osimertinib (AZD9291), Almonertinib, Alflutinib (also known as Furmonertinib), EAI045, JBJ-25-02, BLU945, BLU701, TOB3804, BBT-176, ES-072, BPI-361175, CH7233163, and a pharmaceutically acceptable salt thereof.

2. The method of claim 1, wherein the pharmaceutically acceptable salt of the IN10018 is tartrate salt.

3. The method of claim 1, wherein the epidermal growth factor receptor tyrosine kinase inhibitor is selected from the group consisting of Osimertinib, Almonertinib, Alflutinib, and a pharmaceutically acceptable salt thereof.

4. The method of claim 1, wherein the IN10018 or a pharmaceutically acceptable salt thereof and the epidermal growth factor receptor tyrosine kinase inhibitor are administered simultaneously or sequentially to the subject.

5. The method of claim 1, wherein the tumor is selected from the group consisting of bladder cancer, breast cancer, cervical cancer, colon cancer (including colorectal cancer), esophageal cancer, esophageal squamous cell carcinoma, head and neck cancer, liver cancer, lung cancer (including small cell lung cancer and non-small cell lung cancer), melanoma, myeloma, rhabdomyosarcoma, inflammatory myofibroblastic tumor, neuroblastoma, pancreatic cancer, prostate cancer, kidney cancer, renal cell carcinoma, sarcoma (including osteosarcoma), skin cancer (including squamous cell carcinoma), gastric cancer, testicular cancer, thyroid cancer, uterine cancer, mesothelioma, cholangiocarcinoma, leiomyosarcoma, liposarcoma, nasopharyngeal carcinoma, neuroendocrine carcinoma, ovarian cancer, salivary gland cancer, metastasis caused by spindle cell carcinoma, anaplastic large cell lymphoma, thyroid undifferentiated carcinoma, non-Hodgkin's lymphoma, Hodgkin's lymphoma, neuroglioma, and hematological malignancies, such as acute myeloid leukemia (AML), acute lymphoblastic leukemia (ALL), diffuse large B-cell lymphoma (DLBCL), follicular lymphoma (FL), chronic lymphocytic leukemia (CLL), and chronic myeloid leukemia (CML).

6. A kit or pharmaceutically acceptable composition comprising:
(a) IN10018 or a pharmaceutically acceptable salt thereof; and
(b) an epidermal growth factor receptor tyrosine kinase inhibitor, wherein the IN10018 has a structure of:

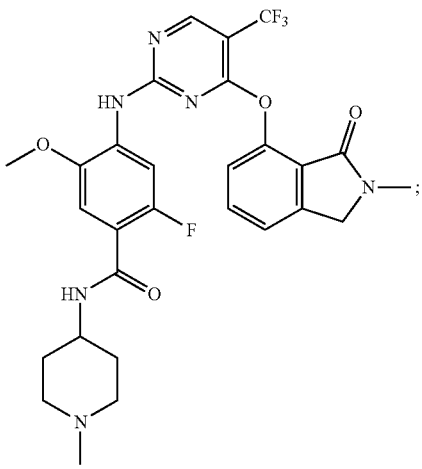

and the epidermal growth factor receptor tyrosine kinase inhibitor is selected from the group consisting of Icotinib, Afatinib, Crizotinib, Osimertinib (AZD9291), Almonertinib, Alflutinib (also known as Furmonertinib), EAI045, JBJ-25-02, BLU945, BLU701, TOB3804, BBT-176, ES-072, BPI-361175, CH7233163, and a pharmaceutically acceptable salt thereof.

7. The kit or composition of claim 6, wherein the epidermal growth factor receptor tyrosine kinase inhibitor is selected from the group consisting of Osimertinib, Almonertinib, Alflutinib, and a pharmaceutically acceptable salt thereof.

8. The kit or composition of claim 6, which is used as a drug.

9. The kit or composition of claim 6, wherein the pharmaceutically acceptable salt of the IN10018 is tartrate salt.

10. The kit or composition of claim 8, which is used as a drug for treating a tumor.

11. The kit or composition of claim 10, wherein the tumor is selected from the group consisting of bladder cancer, breast cancer, cervical cancer, colon cancer (including colorectal cancer), esophageal cancer, esophageal squamous cell carcinoma, head and neck cancer, liver cancer, lung cancer (including small cell lung cancer and non-small cell lung cancer), melanoma, myeloma, rhabdomyosarcoma, inflammatory myofibroblastic tumor, neuroblastoma, pancreatic cancer, prostate cancer, kidney cancer, renal cell carcinoma, sarcoma (including osteosarcoma), skin cancer (including squamous cell carcinoma), gastric cancer, testicular cancer, thyroid cancer, uterine cancer, mesothelioma, cholangiocarcinoma, leiomyosarcoma, liposarcoma, nasopharyngeal carcinoma, neuroendocrine carcinoma, ovarian cancer, salivary gland cancer, metastasis caused by spindle cell carcinoma, anaplastic large cell lymphoma, thyroid undifferentiated carcinoma, non-Hodgkin's lymphoma, Hodgkin's lymphoma, neuroglioma, and hematological malignancies, such as acute myeloid leukemia (AML), acute lymphoblastic leukemia (ALL), diffuse large B-cell lymphoma (DLBCL), follicular lymphoma (FL), chronic lymphocytic leukemia (CLL), and chronic myeloid leukemia (CML).

12. The method of claim 5, wherein the tumor is selected from the group consisting of lung cancer, breast cancer, neuroglioma, esophageal cancer, head and neck cancer, and colon cancer.

13. The method of claim 12, wherein the tumor is lung cancer or colon cancer.

14. The kit or composition of claim 11, wherein the tumor is selected from the group consisting of lung cancer, breast cancer, neuroglioma, esophageal cancer, head and neck cancer, and colon cancer.

15. The kit or composition of claim 14, wherein the tumor is lung cancer or colon cancer.

* * * * *

UNITED STATES PATENT AND TRADEMARK OFFICE
CERTIFICATE OF CORRECTION

PATENT NO. : 11,986,477 B2
APPLICATION NO. : 18/387180
DATED : May 21, 2024
INVENTOR(S) : Baoyuan Zhang et al.

It is certified that error appears in the above-identified patent and that said Letters Patent is hereby corrected as shown below:

In the Claims

At Column 32, Claim number 1, Line number 27, delete "TOB3804" and insert --TQB3804--.
At Column 33, Claim number 6, Line number 29, delete "TOB3804" and insert --TQB3804--.

Signed and Sealed this
Second Day of July, 2024

Katherine Kelly Vidal
Director of the United States Patent and Trademark Office